United States Patent
Cossio et al.

(10) Patent No.: US 8,097,656 B2
(45) Date of Patent: Jan. 17, 2012

(54) NITROGENATED TRANS-STILBENE ANALOGS, METHOD FOR THE OBTENTION AND MEDICAL APPLICATIONS THEREOF

(75) Inventors: Fernando Pedro Cossio, Leioa (ES); Eneko Aldaba Arevalo, Leioa (ES); Yosu Ion Vara Salazar, Leioa (ES); Aizpea Zubia Olascoaga, Leioa (ES); Silvia Vivanco Amato, Leioa (ES); Miren Lorea Mendoza Arteche, Derio (ES); Clarisa Salado Pogonza, Derio (ES); Natalia Gallot Escobal, Derio (ES); Fernando Vidal Vanaclocha, Derio (ES)

(73) Assignees: Dominion Pharmakine S.L, Derio (ES); Universidad del Pais Vasco, Leiona (ES)

( * ) Notice: Subject to any disclaimer, the term of this patent is extended or adjusted under 35 U.S.C. 154(b) by 0 days.

(21) Appl. No.: 12/861,581

(22) Filed: Aug. 23, 2010

(65) Prior Publication Data
US 2011/0060038 A1 Mar. 10, 2011

Related U.S. Application Data

(63) Continuation of application No. 11/918,478, filed as application No. PCT/EP2006/061565 on Apr. 12, 2006, now abandoned.

(60) Provisional application No. 60/671,669, filed on Apr. 15, 2005.

(51) Int. Cl.
*A61K 31/137* (2006.01)
*C07C 251/24* (2006.01)

(52) U.S. Cl. ........................................ 514/641; 564/274
(58) Field of Classification Search .................. 514/641; 564/248
See application file for complete search history.

(56) References Cited

U.S. PATENT DOCUMENTS
2008/0262073 A1 10/2008 Cossio Mora et al.

FOREIGN PATENT DOCUMENTS
WO WO 93/23357 11/1993
WO WO 93/23364 11/1993

OTHER PUBLICATIONS

Lala et al., Role of nitric oxide in tumor progression: Lessons from experimental tumors, Cancer and Metastasis Reviews (1998), 17,91-106.
Golub et al., Molecular Classification of Cancer: Class Discovery and Class Prediction by Gene Expression Monitoring, Science (1999), vol. 286,531-537.
Kim et al., Antiproliferative Effect of Resveratrol in Human Prostate Carcinoma Cells, Journal of Medicinal Food, vol. 6, No. 4, pp. 273-280, 2003.
Cushman, et al. Synthesis and Evaluation of a Series of Benzylaniline Hydrochlorides as Potential Cytotoxic and Antimitotic Agents Acting by Inhibition of Tubulin Polymerization, J. Med, Chem, vol. 36, pp. 2817-2821,1993.
Heo et al., "Induction of quinons reductase activity by Stilbene Analogs in Mouse Hepa 1c1c7 Cells" Chemical Abstracts Service, Pharmaceutical Society of Korea, 2001.
Sun et al., "Examination of the 1,2 disubstituted azetidinone ring system as a template for combretastatin A-4 conformationally restricted analogue design", Chemical Abstracts Service, Elsevier Science B.V 2004.
Galyzmetdinova, et al., "Copper complexes with 4,4-dialkoxy-2-hydroxybenzalaniline as liquid crystal paramagnetic spin probes and 4,4-dialkoxy-2-hydroxybenzalanilines", Chemical Abstracts Service, Physical-Technical Institute, Apr. 15, 1984.
Yoo et al., "Patent Inhibitory Effects of Resveratrol Derivatives on Progression of Prostate Cancer Cells", Chemical Abstracts Service, Archiv Der. Pharmazie, Germany 2006.
Kim et al., "Design, Synthesis, and Discovery of Novel trans-Stilbene Analogues as Potent and Selective Human Cytochrome 1B1 Inhibitors", J. Med. Chem, vol. 45, pp. 160-164,2002.
Aggarawal, et al. "Role of Resveratrol in Prevention and Therapy of Cencer: Preclinical and Clinical Studies", Anticancer Research, vol. 24, pp. 2783-2840, 2004.

*Primary Examiner* — Kamal Saeed
*Assistant Examiner* — Kristin Bianchi
(74) *Attorney, Agent, or Firm* — Leason Ellis LLP

(57) ABSTRACT

This invention is related to new nitrogenated trans-stilbene compounds, more specifically, imine, pyrrole and indole derivatives, with procedures for the preparation and use thereof as pharmaceutical compositions for the treatment and/or chemoprevention of those mammalian diseases such as cancer, fibrosclerosis and acute/chronic inflammation, graft-versus-host reaction, ischemic-reperfusion tissue injury in stroke and heart attack, neurodegeneration, and during organ transplantation, whose pathogenic and pathophysiological mechanisms depend on or are significantly contributed by undesirable oxidative stress, angiogenic and proliferative responses.

9 Claims, 11 Drawing Sheets

NITROGENATED TRANS-STILBENE ANALOGS, METHOD FOR THE OBTENTION AND MEDICAL APPLICATIONS THEREOF

This patent application is a continuation of U.S. application Ser. No. 11/918,478 filed on Jun. 8, 2009 now abandoned, entitled "New Nitrogenated Trans-stilbene Analogs, Method for the Obtention and Medical Applications Thereof," which is a national stage filing under 35 U.S.C. §371 of International Application No. PCT/EP2006/061565 filed Apr. 12, 2006, which claims the benefit of priority of U.S. Provisional Application Ser. No. 60/671,669, filed on Apr. 15, 2005. The contents of all prior applications are hereby incorporated by reference in their entirety herein.

This invention is related to new nitrogenated trans-stilbene analog compounds, more specifically, imine, pyrrol and indole derivatives, with procedures for the preparation and use thereof as pharmaceutical compositions for the treatment and/or chemoprevention of those mammalian diseases such as cancer, fibrosclerosis and acute/chronic inflammation, graft-versus-host reaction, ischemic-reperfusion tissue injury in stroke and heart attack, neurodegeneration, and during organ transplantation, whose pathogenic and pathophysiological mechanisms depend on or are significantly contributed by undesirable oxidative stress, angiogenic and proliferative responses.

BACKGROUND OF THE INVENTION

It is known that the chemical synthesis of aromatic imines (or Schiff bases) can generally be achieved by means of the condensation between primary amines and carbonylic compounds (cf. Patai, *The Chemistry of Carbon—Nitrogen Double Bond*; Wiley: New York, 1970, pp. 64).

Likewise, polysubstituted pyrrol rings can be chemically synthesized in different ways by employing linear or convergent synthesis methodologies (cf. Sundberg, *Comprehensive Heterocyclic Chemistry*; Katrizki, A. and Rees, C. W. Eds.; Pergamon: Oxford, 1984; vol. 4, pp. 313). One sufficiently general way consists of the aromatization of substituted pyrrolidines (cf. Fejes et al. *Tetrahedron* 2000, vol. 56, pp. 8545; Gupta et al. *Synth. Commun.* 1998, vol. 28, pp. 3151). The final heterocycles can be prepared, in turn, by means of the 1,3-dipolar reaction between azomethine ylides and electronically deficient alkenes (cf. Ayerbe et al. *J. Org. Chem.* 1998, vol. 63, pp. 1795; Vivanco et al. *J. Am. Chem. Soc.* 2000, vol. 122, pp. 6078).

Methods also abound for the synthesis of indoles (cf. Horton et al. *Chem. Rev.* 2003, vol. 103, pp. 893), one of which is a convergent procedure described in literature consisting of the thermal cyclation between primary arylamines and haloacetopheonone derivatives (cf. Nyerges et al. *Tetrahedron Lett.* 2005, vol. 46, pp. 377). However, the yields obtained by this method are not usually very high, due mainly to the relatively high temperatures and the lengthy reaction times necessary for completing the cyclation reaction and the ease with which the reagents may degrade under these conditions.

Oxidative stress facilitates carcinogenesis (Engel R H, Evens A M. Oxidative stress and apoptosis: a new treatment paradigm in cancer. Front Biosci. 2006; 11:300-12) and the prometastatic and proangiogenic mechanisms of cancer (Tanaka T, Akatsuka S, Ozeki M, Shirase T, Hiai H, Toyokuni S. Redox regulation of annexin 2 and its implications for oxidative stress-induced renal carcinogenesis and metastasis. Oncogene. 2004; 23:3980-9) and many other diseases (Casetta I, Govoni V, Granieri E. stress, antioxidants and neurodegenerative diseases. Curr Pharm Des. 2005; 11(16):2033-52; Sukkar S G, Rossi E. Oxidative stress and nutritional prevention in autoimmune rheumatic diseases. Autoimmun Rev. 2004; 3:199-206; Naito Y, Takano H, Yoshikawa T. Oxidative stress-related molecules as a therapeutic target for inflammatory and allergic diseases. Curr Drug Targets Inflamm Allergy. 2005; 4:511-5.). Thus, numerous cancer research studies have focused their attention on the effects of some natural antioxidant compounds (resveratrol, quercetin, vitamin C, etc.) as chemopreventive agents of carcinogenesis and metastasis. In come cases, it has been proven that said action is caused not solely by means of the antioxidant effect of said agents, but also by way of their action of blocking cyclooxygenases (COX) and tyrosine kinases.

On the other hand, the mechanism of action of most of the proinflammatory and prometastatic factors is regulated by oxygen-reactive metabolites. In this regard, it has been proven that treating animals with catalase prior to their being intrasplenically inoculated with B16 melanoma cells reduces the onset of hepatic metastasis, which indicates that hydrogen peroxide (H2O2), released in response to hepatic colonization by tumor cells, has prometastatic effects (cf. Anasagasti et al., "*Sinusoidal endothelium release of hydrogen peroxide enhances very late antigen*—4-mediated melanoma cell adherence and tumor cytotoxicity during interleukin-1 promotion of hepatic melanoma metastasis in mice". *Hepatology.* 1997, vol. 25 pp. 840-6).

Trans-stilbene compounds, particularly trans-resveratrol, are widespread throughout nature, mainly in the form of phytoalexins and are attracting growing interest due to a wide range of biological activities useful in oncology, such as the inhibition of carcinogenesis (cf. Jang et al., *Science* 1997, vol. 275, pp. 218; Gosslan et al., *Brit. J. Cancer.* 2005, vol. 92, pp. 513) and apoptosis induction (cf. Lee et al., *Life Sci.* 2004, vol. 75, pp. 2829). This biological activity has been attributed to the antioxidant properties (cf. Stivala et al., *J. Biol. Chem.* 2001, vol. 276, pp. 22586) and anti-inflammatory properties (cf. Kimura et al., *Biochim. Biophys. Acta* 1985, vol. 834, pp. 275) of these compounds, as a result of which they can serve as chemopreventive and chemotherapeutic agents (cf. De Lédinghen et al., *Int. J. Oncol.* 2001, vol. 19, pp. 83; Scheneider et al., *Nutr. Cancer* 2001, vol. 39, pp. 102; Mahyer-Roemer et al., *Int. J. Cancer* 2001, vol. 94, pp. 615). It is known that trans-stilbenes are able to isomerize the cis-form which is either inactive or less active. For example, trans-resveratrol can isomerize under the effect of sunlight to convert partially into the cis isomer (cf. F. Olalla, *Curr. Med. Chem.* 2006, vol 13, pp. 87-98; 1. Kolouchová-Hanzliková et al. *Food Chem.* 2004, vol. 87, pp. 151-158).

DESCRIPTION OF THE INVENTION

Brief Description of the Invention

The invention described herein is related to nitrogenated polyhydroxylated and/or polyalcoxylated trans-stilbene analog compounds, which include imine derivatives, pyrrol derivatives or indole derivatives, useful as inhibitors of inflammatory agents, oxidative stress, angiogenesis-related effects, metastasis and cancer progression. This invention is also related to therapeutic compositions which include said compounds and the use thereof for the treatment and prophylaxis of cancerous and inflammatory diseases, such as, but not limited to, cancer metastasis. This invention is also related to the methods for obtaining said compounds.

Figure 2:
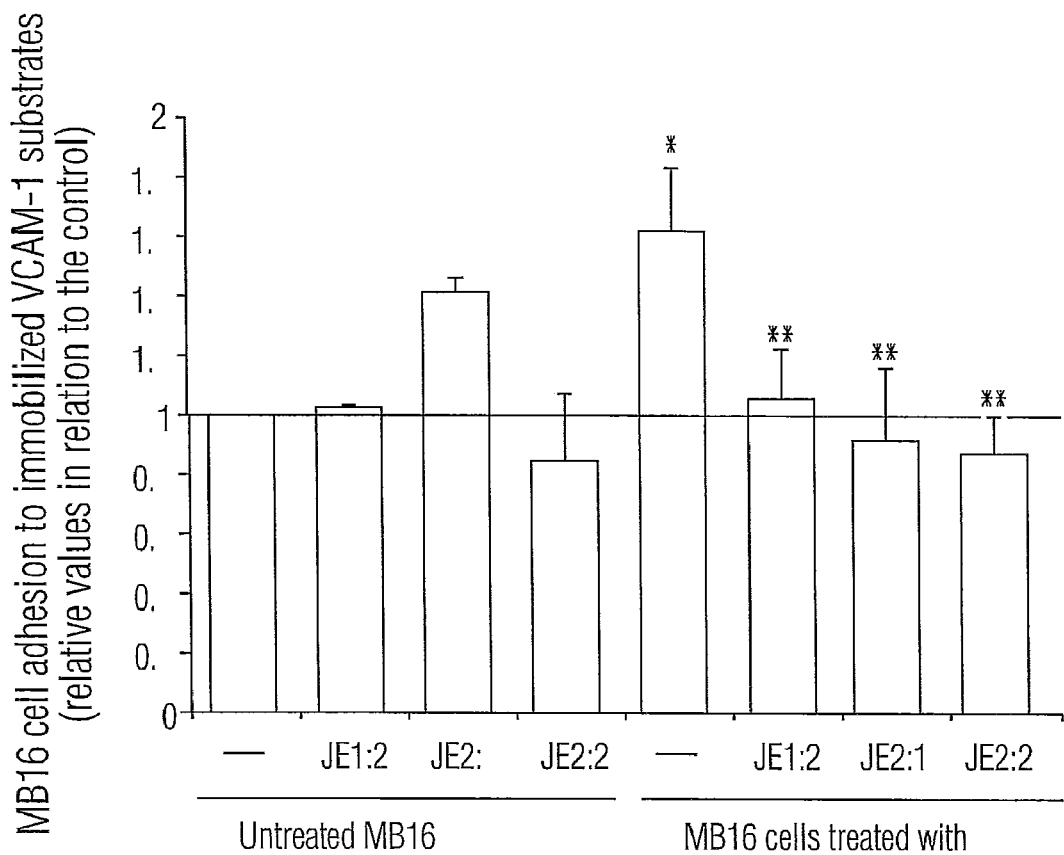

FIG. 2.—Shows the inhibitory effect of the compounds JE1:2, JE2:1 and JE2:2 on the adhesion of the murine B16 melanoma (MB16) cells treated or not with non-toxic concentrations of H2O2 to immobilized recombinant VCAM-1 substrates. The differences in adhesion with regard to the untreated MB16 cells (*) and the MB16 cells treated with H2O2 (**) are statistically significant (P<0.01) according to Student's t-test.

Figure 3:
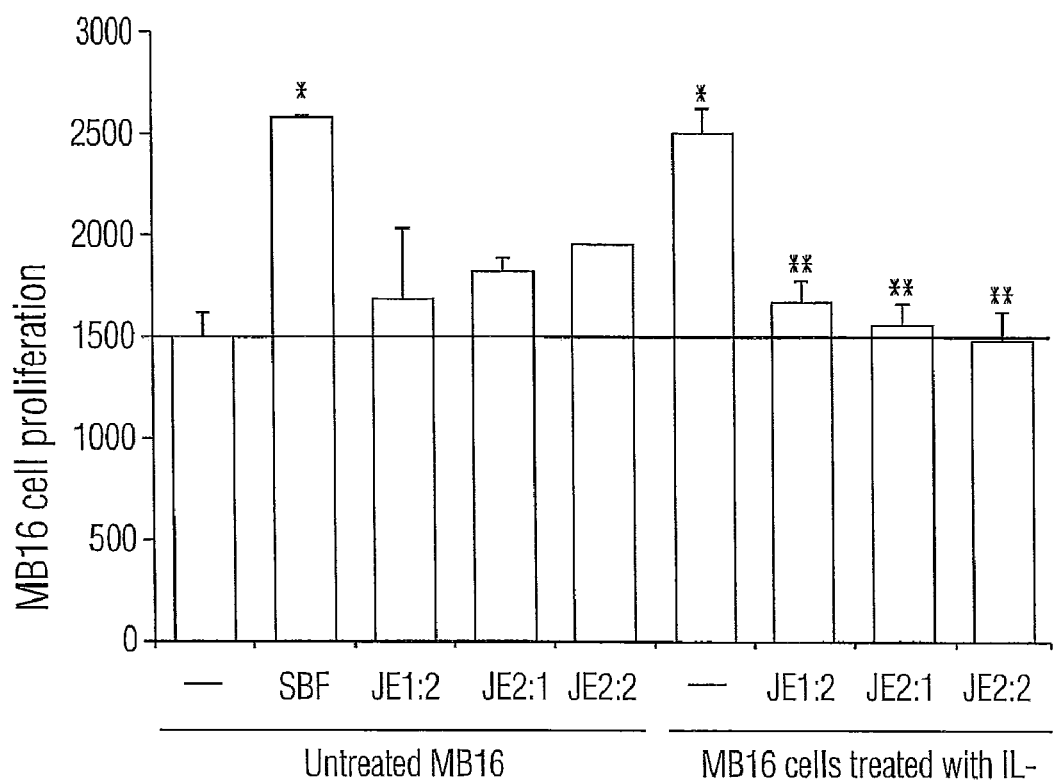

FIG. 3.—Shows the inhibitory effect of the compounds JE1:2, JE2:1 and JE2:2 on the in vitro proliferation of MB16 cells treated or not with recombinant IL-18. The differences in proliferation with regard to the untreated MB16 cells (*) and the MB16 cells treated with IL-18 (**) are statistically significant (P<0.01) according to Student's t-test.

Figure 4:
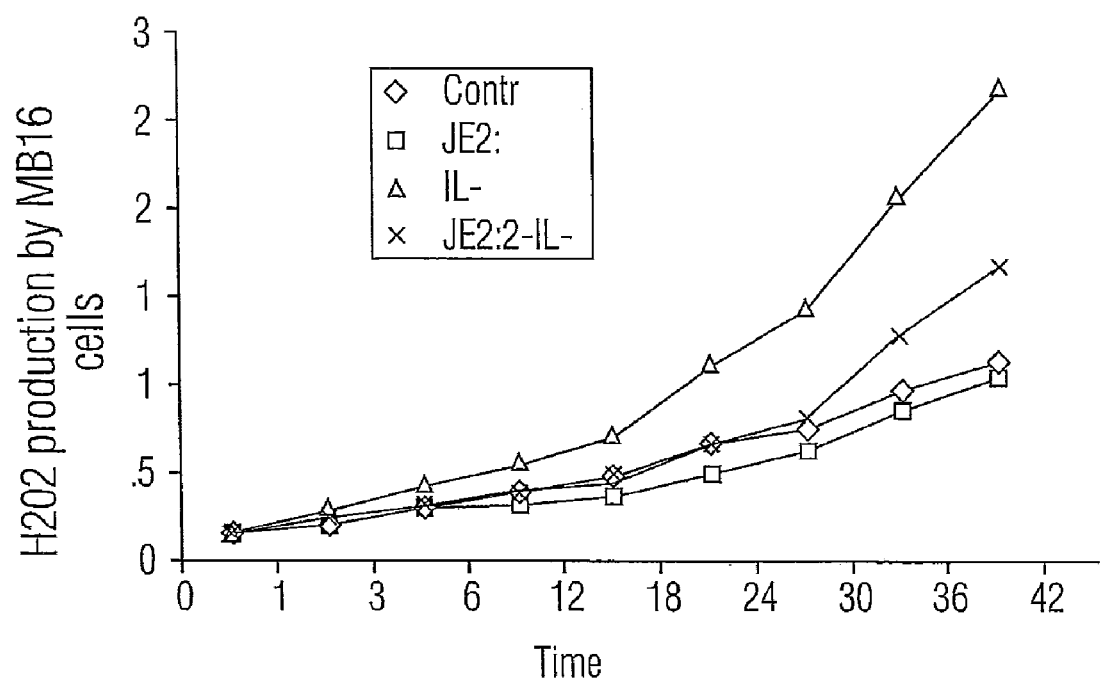

FIG. 4.—Shows the inhibitory effect of the compound JE2:2 on the production of H2O2 from MB16, treated or not with recombinant IL-18 in vitro.

Figure 5:
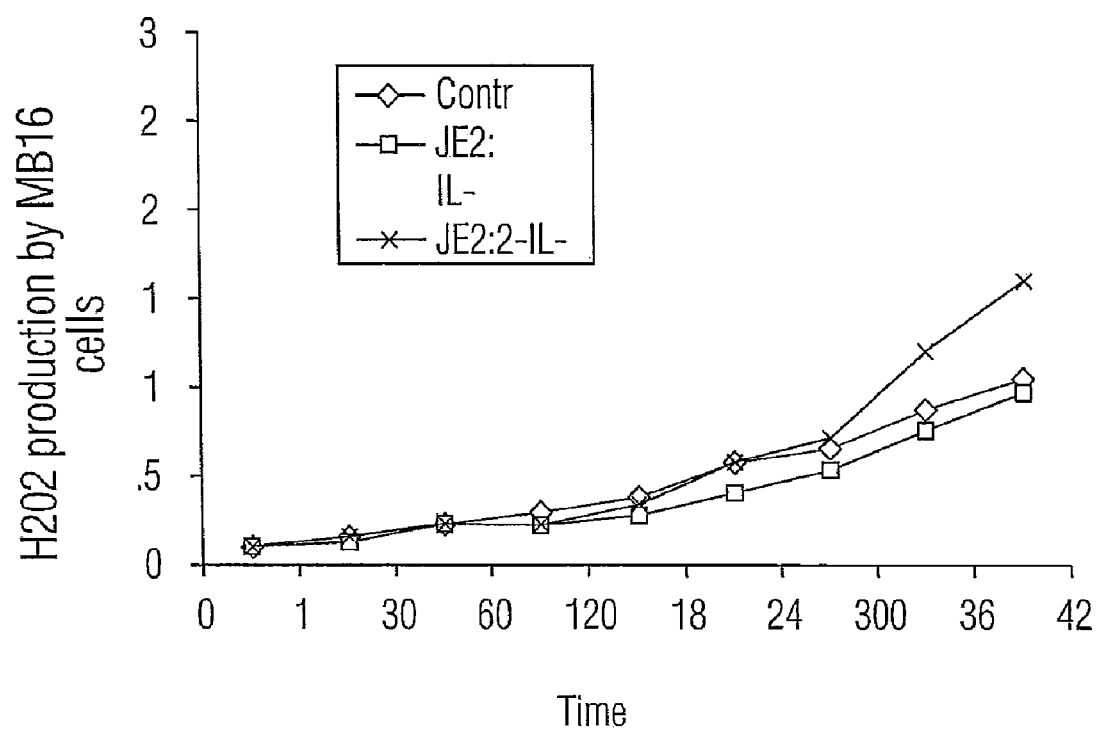

FIG. 5.—Shows the inhibitory effect of the compounds JE1:2, JE2:1 and JE2:2 on the production of H2O2 from primary cultured mouse hepatic sinusoidal endothelium (HSE) cells.

Figure 6:
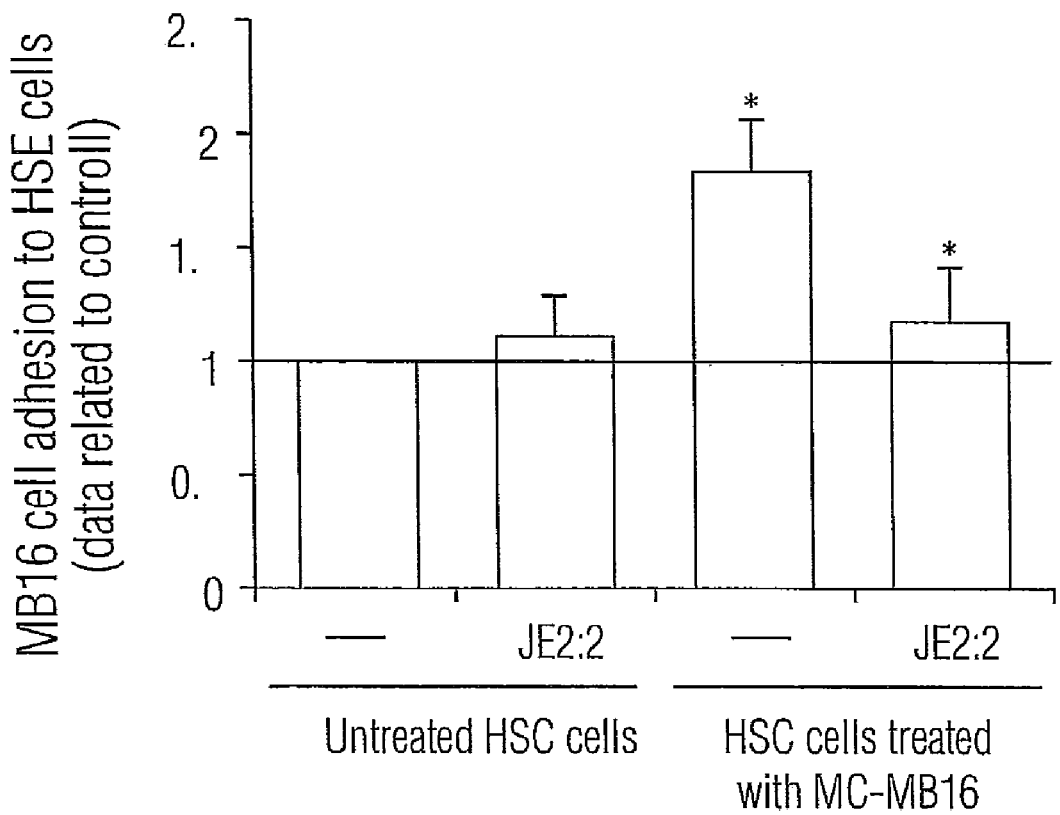

FIG. 6.—Shows the inhibitory effect of the compound JE2:2 on the adhesion of MB16 cells to the primary cultured mouse HSE cells treated or not with MB16 conditioned media (MC-MB16). The differences in adhesion with regard to the untreated HSE cells (*) and the HSE cells treated with MC-MB16 (**) are statistically significant (P<0.01) according to Student's t-test.

Figure 7:
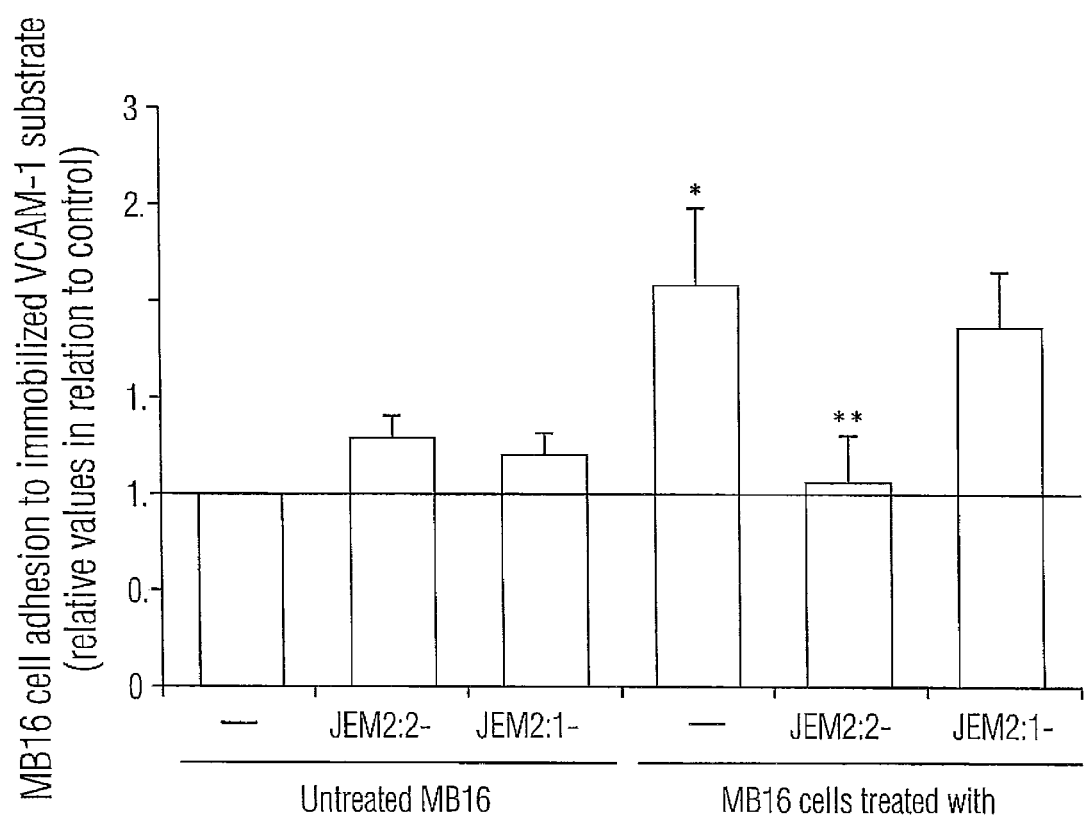

FIG. 7.—Shows the effects of the compounds JE2:2-01 and JE2:1-02 on the adhesion of the MB16 cells treated or not with H2O2 to immobilized VCAM-1 substrates. The differences in adhesion with regard to the untreated MB16 cells (*) and the MB16 cells treated with H2O2 (**) are statistically significant (P<0.01) according to Student's t-test.

Figure 8:
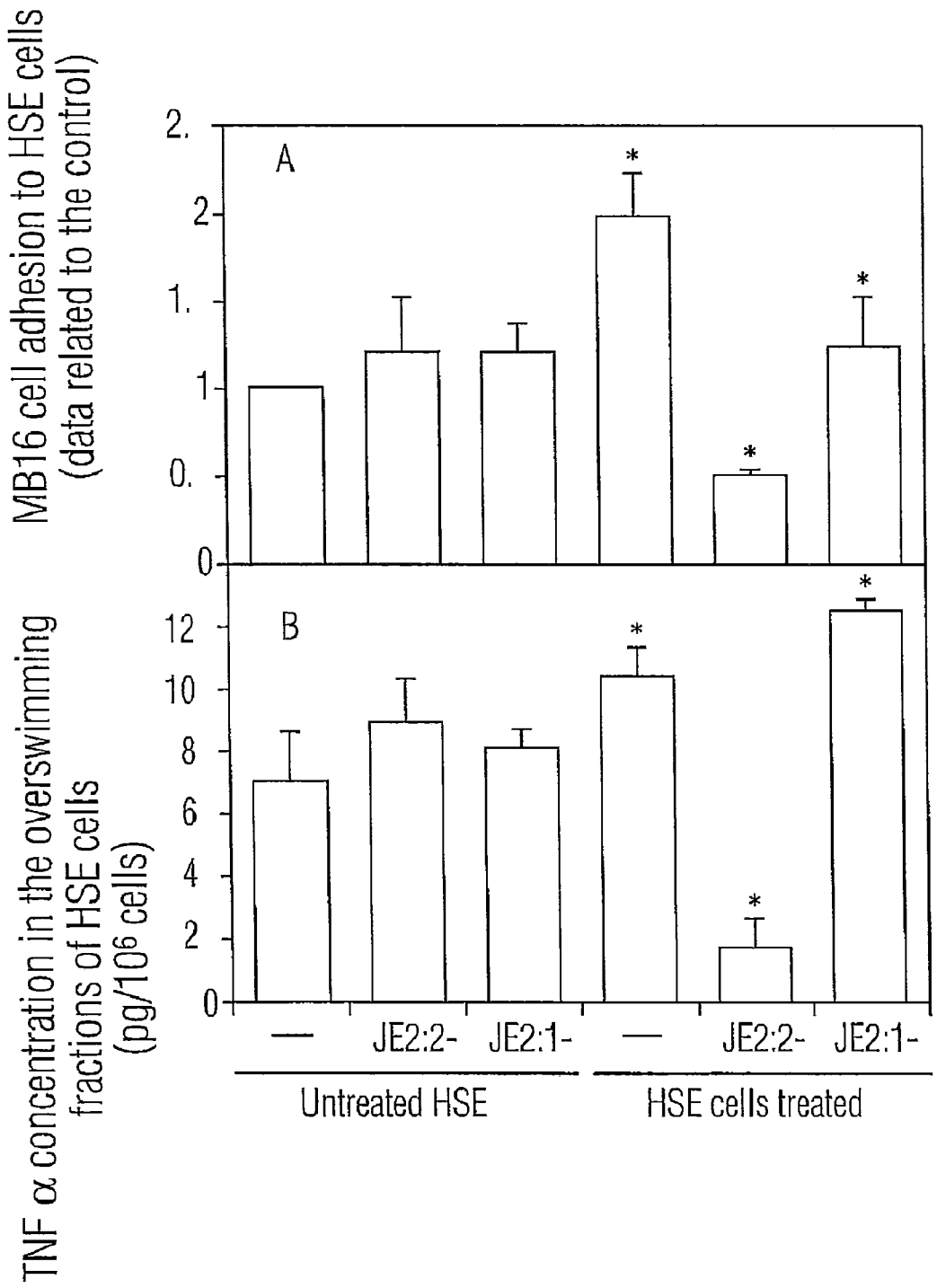

FIG. 8.—Shows the inhibitory effect of JE2:2-01 and JE2:1-02 (A) on the adhesion of MB16 cells and (B) on the production of TNF-alpha from HSE cells treated or not with MC-MB16. The differences in the adhesion or in the concentration of TNF-alpha with regard to the untreated HSE cells (*) and the HSE cells treated with MC-MB16 (**) are statistically significant (P<0.01) according to Student's t-test.

Figure 9:
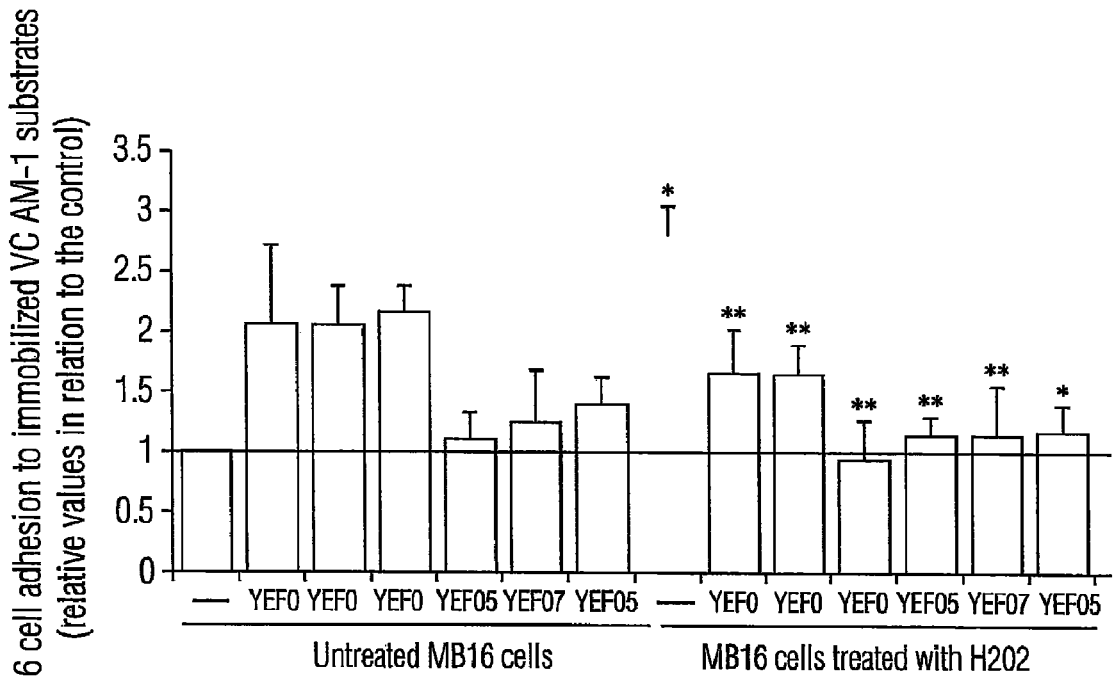

FIG. 9.—Shows the inhibitory effect of the compounds YEF02, YEF03, YEF07, YEF05B, YEF07B and YEF05H on the adhesion of MB16 cells treated or not with H2O2 to immobilized VCAM-1 substrate. The differences in adhesion between untreated MB16 cells (*) and H2O2-treated MB16 cells (**) are statistically significant (P<0.01) according to Student's t-test.

Figure 10:
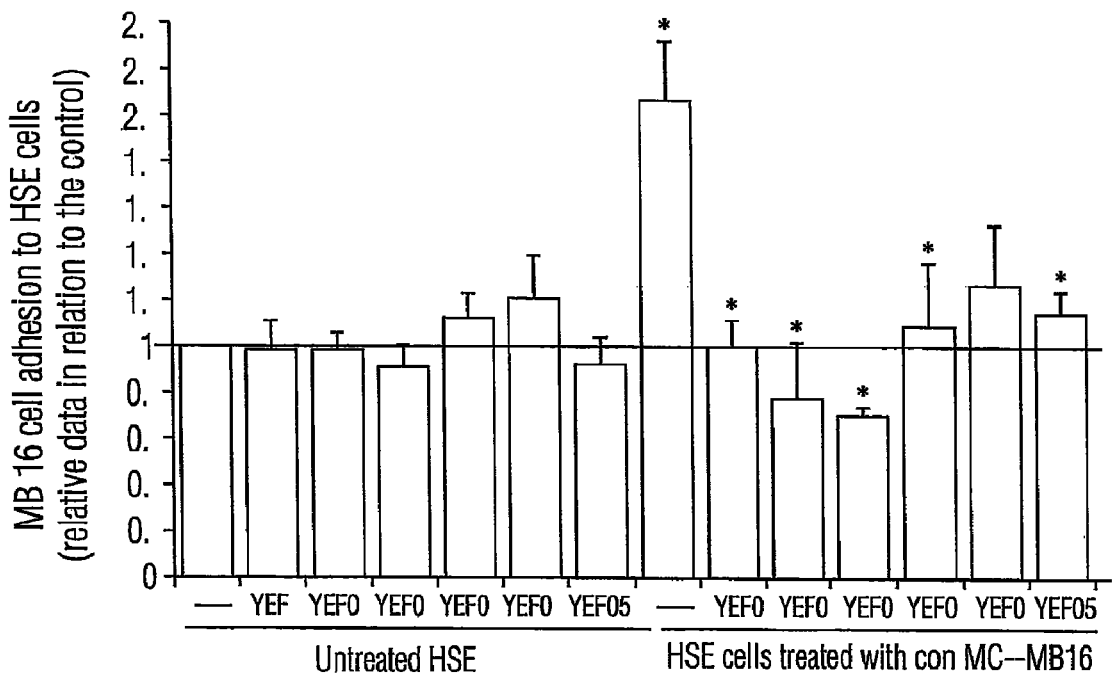

FIG. 10.—Shows the inhibitory effect of the compounds YEF02, YEF03, YEF07, YEF05B, YEF07B and YEF05H on the adhesion of MB16 cells to HSE treated or not with MC-MB16. The differences in adhesion with regard to untreated (4) and the MC-MB16-treated (**) HSE cells are statistically significant (P<0.01) according to Student's t-test.

Figure 11:
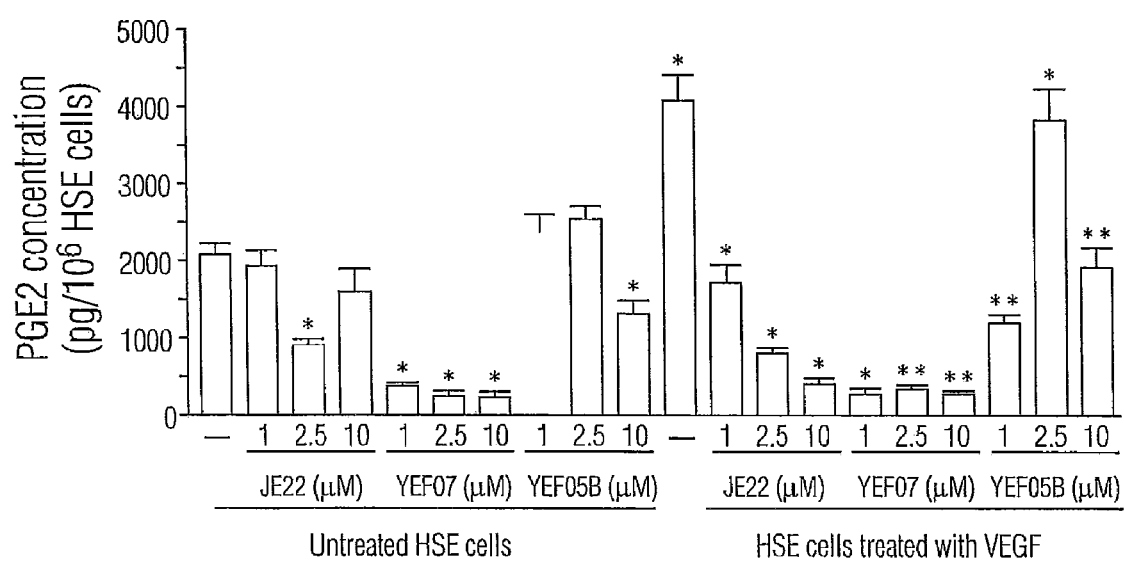

FIG. 11.—Shows the inhibitory effect of the compounds JE22, YEF07 and YEF05B on the production of PGE2 (as evidence of cyclooxygenase-2 activity) by HSE cells in response to VEGF. The differences in the PGE2 production between untreated (*) and VEGF-treated (**) HSE cells are statistically significant (P<0.01) according to Student's t-test.

Figure 12:
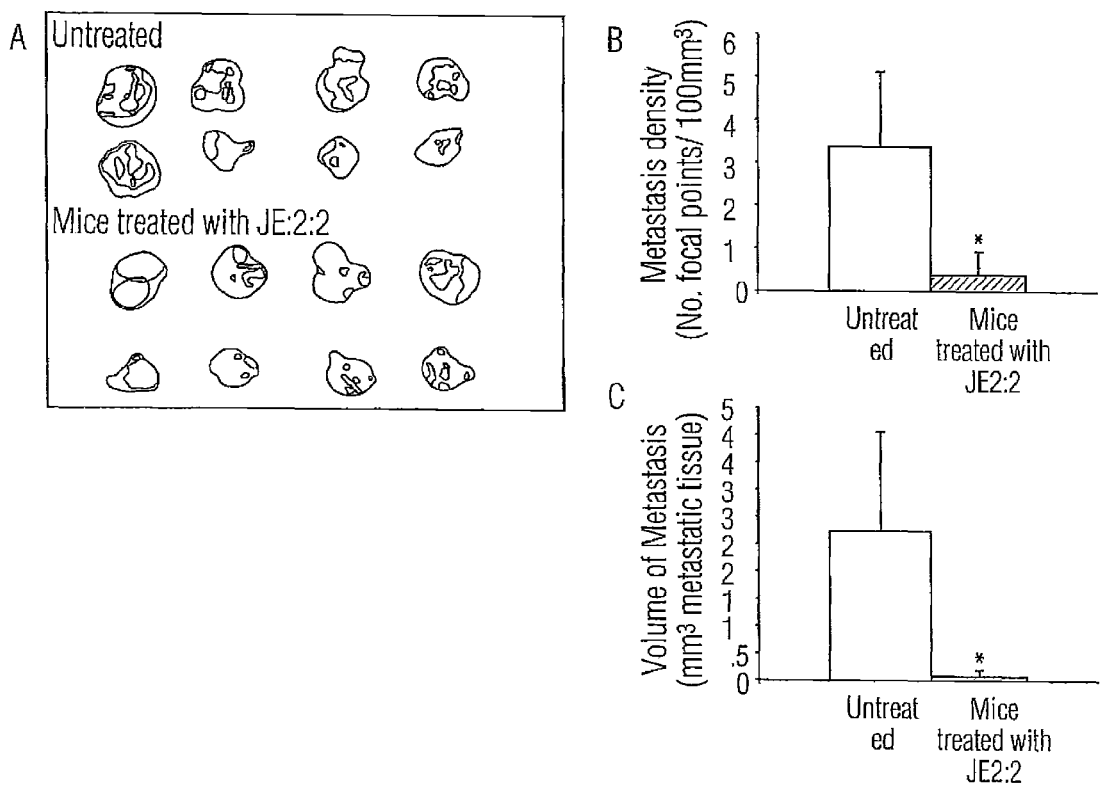

FIG. 12A, FIG. 12B y FIG. 12 C.—Effect of the compound JE2:2 on the development of hepatic metastasis following the intrasplenic injection of basal medium-cultured MB16 cells in C57BL/6J mice.

DETAILED DESCRIPTION OF THE INVENTION

According to the first aspect of the invention described herein, a nitrogenated compound of polyhydroxylated and/or polyaloxylated trans-stilbene is provided with the following general formula (I):

$$\begin{array}{c} R^2 \quad R^1 \quad\quad R^6 \quad R^7 \\ R^3-\!\!\!\diagdown\!\!A\!\!\diagup\!\!-X-\!\!\diagdown\!\!B\!\!\diagup\!\!-R^8 \\ R^4 \quad R^5 \quad\quad R^{10} \quad R^9 \end{array} \quad (I)$$

or any of the salts thereof, where:
(X) is selected from between the following groups, imine or pyrrole:

$$\underset{\text{(imine group)}}{D\!\!\diagup\!\!=\!\!N\!\!\diagdown\!\!U} \qquad \underset{\text{(pyrrole group)}}{\overset{Y\quad U}{\underset{Z}{D\!\!\diagdown\!\!N\!\!\diagup\!\!W}}}$$

In the case in which the group (X) is a pyrrole group, it may be bonded to the phenyl group (A) by one or two of its pyrrole ring carbons. When it is bonded by two of its carbons, then (D) and (Y) form part of the ortho-disubstituted phenyl group (A);
(D) is the phenol ring (A) (aromatic ring (A) of the general structure (1);
(U) may be selected from among a hydrogen atom, a linear or branched alkyl group ($C_1$-$C_{10}$) or the phenyl group (B) (aromatic ring (B) of general formula (I);
(Y) may be selected from among a hydrogen atom or a group selected from among nitro ($NO_2$), amino ($NR_2$), linear or branched alkoxycarbonyl (—C(═O)OR), amide (NRC(═O)R') or an organic or inorganic quaternary ammonium salt ($NR_4^+$), such as, for example but not limited to, quaternary ammonium chloride or tartrate;
(Y) does not exist when the carbon to which it is bonded forms part of the phenyl A ortho-disubstituted group
(W) may be selected from among a hydrogen atom or a group selected among carboxyl (—C(═O)OR) or aminocarbonyl [(C(═O)NRR') mono or disubstituted for alkyl, aryl or heteroaryl groups] oe (W) is the phenyl group (B) (aromatic ring (B) of general formula (I)
(Z) may be selected from among a hydrogen atom or a group selected from among a linear or branched alkyl ($C_1$-$C_{10}$), benzyl (—$C_6H_5$), carboxyl and analogs (—C(═O)OR), arylakyl, heteroarylmethyl, O-alkyl(aryl)carbamoyl or N-alkyl (aryl)semicarbazide.
$R^1$, $R^2$, $R^3$, $R^4$, $R^5$, $R^6$, $R^7$, $R^8$, $R^9$ and $R^{10}$ may be the same or different and are selected from among a hydrogen atom or a group selected between alkoxy (—OR) and hydroxyl (—OH), where at least three of these substitutes are either alkoxy and/or hydroxyl.
$R^5$ is absent when the pyrrole ring is bonded to ring (A) by two of its carbon atoms.

In the invention described herein, the term "alkyl" $C_1$-$C_{10}$, is a saturated linear or branched-chain hydrocarbon which includes from 1 to 10 carbon atoms. The alkyl groups preferred in this invention are, but are not limited to, those which have 1 to 5 carbon atoms, for example, the methyl, ethyl, propyl, isopropyl, butyl, isobutyl, sec-butyl, tert-butyl, pentyl and isopentyl groups.

The term "alkoxy" means an (—OR) radial, where R is a linear or branched alkyl chain of 1 to 10 carbon atoms. The alkoxy groups preferred in this invention are, but are not limited to, those having 1 to 5 carbon atoms, such as, for example, methoxyl, etoxyl, propoxyl, isopropoxyl, butoxyl, pentoxyl, sec-butoxyl or tert-butoxyl.

The term "amine" means a radical (—$NR_2$), where the two R groups may be the same or different and represent a hydrogen atom or a linear or branched alkyl chain of 1 to 10 carbon atoms. The amino groups preferred in this invention are, but are not limited to, those in which both R are hydrogen of any thereof is an alkyl chain of 1 to 5 carbon atoms, more preferably of 1 or 2 carbon atoms.

The term "arylalkyl" means a linear or branched chain of 1 to 5 carbon atoms which is substituted by an aryl radical, where the term "aryl", in this invention, means a substituted or non-substituted phenyl radical. The group is preferably, but not limited to, an arylmethyl.

The term "heteroarylalkyl" means a linear or branched chain or 1 to 5 carbon atoms which is substituted by an aromatic radical of 5 or 6 bonds with one, two or three heteroatoms, understood as being the elements nitrogen, oxygen and sulfur.

The term "carboxyl" (—C(=O)OR) encompasses a carboxylic acid (R=H) and an ester in which R may be a linear or branched alkyl group (linear or branched "alkoxycarbonyl"), or a cyclic alkyl group.

The term "amide" means a radical with the form (—NCR(=O)R') where the R and R' groups may be the same or different and represent an atom of hydrogen or a linear or branched alkyl chain of 1 to 10 carbon atoms. The amide groups preferred in this invention are, but are not limited to, those in which both R's are hydrogen and one thereof is an alkyl chain of 1 to 5 carbon atoms, more preferably of 1 or 2 carbon atoms.

The term "aminocarbonyl" means a radical with the form (—C(=O)NRR') where the R and R' groups may be the same or different and represent a hydrogen atom or a linear or branched alkyl chain of 1 to 10 carbon atoms or an aryl or a heteroaryl group.

In one preferred embodiment of the invention described herein, a formula (II) compound is provided, which is obtained on substituting (X) in the general formula (I) with an imine group:

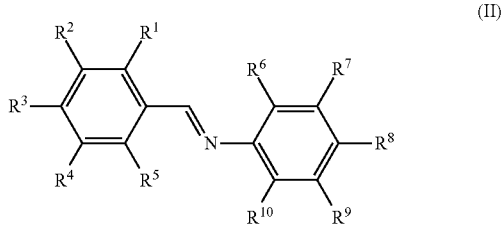

(II)

or any of the salts thereof, where:
$R^1$, $R^2$, $R^3$, $R^4$, $R^5$, $R^6$, $R^7$, $R^8$, $R^9$ and $R^{10}$ are of the same meaning as previously stated hereinabove for the general formula (I).

In a more preferred embodiment of the invention described herein, the general formula (II) compound is, but is not limited to, 5-((E)-(4-Hydroxyphenylimine)methyl)benzene-1,3-diol.

In another preferred embodiment of the invention described herein, a compound with the formula (III) is provided, which is obtained on substituting (X) in the general formula (I) with a pyrrole group:

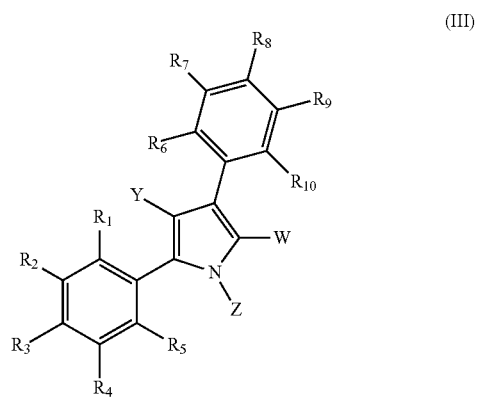

(III)

or any of the salts thereof, where
$R^1$, $R^2$. $R^3$, $R^4$, $R^5$, $R^6$, $R^7$, $R^8$, $R^9$, $R^{10}$ and group (Z) are of the same meaning as previously stated hereinabove for the general formula (I);

(Y) may be selected from among a hydrogen atom or a group selected from among nitro ($NO_2$), amine ($NR_2$), linear or branched alkoxycarbonyl (—C(=O)OR), amide (—C(=O)N—RR') or aminocarbonyl NRC(=O)R') or an organic or inorganic quaternary ammonium salt ($NR_4$'), such as, for example, but not limited to, quaternary ammonium chloride or tartrate;

(W) may be selected from among a hydrogen atom or a group selected between carboxyl (—C(=O)OR) or aminocarboxyl (—C(=O)NRR').

One preferred embodiment of the invention described herein entails a general formula (III) compound where (Z) is a hydrogen atom; (W) is a group selected between —$COOCH_3$ or —COOH; (Y) is a hydrogen atom or a group selected between —$NH_2$ or —$NO_2$; $R^1$, $R^5$, $R^6$ are $R^{10}$ a hydrogen atom; and $R^2$, $R^3$, $R^4$, $R^7$, $R^8$ and $R^9$ are the same or different and represent a hydrogen atom or a group selected between —$OCH_3$ or —OH.

A more preferred embodiment of the invention described herein entails a general formula (III) compound where (Z) and (Y) are hydrogen atoms.

An even more preferred embodiment of the invention described herein entails a general formula (III) compound selected, but without limitation, from among the following group: 3-(4-methoxyphenyl)-5-(dimethoxyphenyl)-1H-pyrol-2-carboxyilic acid, 3,5-bis(3,5-Dihydroxyphenyl)-1H-pyrol-2-methyl carboxylate, 3,5-bis(3,5-Dimethoxyphenyl)-1H-pyrol-2-methyl carboxylate, 5-(3,5-Dihydroxyphenyl)-3-(4-hydroxyphenyl)-1H-pyrol-2-methy 1 carboxylate, 5-(3,5-dimethoxyphenyl)-3-(4-methoxyphenyl)-1H-pyrol-2-methy 1 carboxylate, 5-(3,5-dimethoxyphenyl)-3-(4-methoxyphenyl)-1H-pyrol-2-methy 1 carboxylate, dimethoxyphenyl)-3-(4-methoxyphenyl)-4-nitro-1H-pyrol-2-carboxylate, 4-amino-3,5-bis(3,5-dimethoxyphenyl)-1H-pyrol-2-methyl carboxylate, 5-(3,5-dimethoxyphenyl)-3-(4-methoxyphenyl)-4-nitro-1H-pyrol-2-methyl carboxylate, 3,5-bis(3,5-dimethoxyphenyl)-4-nitro-1H-pyrol-2-methyl carboxylate, 3,5-bis(3,5-dimethoxyphenyl)-1H-pyrol-2-carboxylic acid, and 3-(3,5-Dihydroxyphenyl)-5-(4-hydroxyphenyl)-1H-pyrol-2-methy 1 carboxylate.

One further embodiment of the invention described herein provides a formula (VI) compound which is obtained on substituting (X) in the general formula (I) with a pyrrole group bonded to the aromatic ring (A) by two of its carbon atoms:

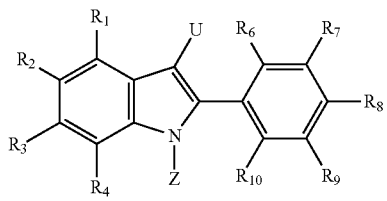

(IV)

or any of the salts thereof, where $R^1, R^2, R^3, R^4, R^6, R^7, R^8, R^9$ and $R^{10}$ and the group (Z) are of the same meaning as previously stated hereinabove for general formula (I); and (U) is hydrogen or a linear or branched $C_1$-$C_{10}$ alkyl group A preferred embodiment of the invention described herein entails a general formula (IV) compound in which (Z) is a hydrogen atom or a —COOC(CH$_3$)$_3$ group; (U) is a hydrogen atom; and $R^1, R^2, R^3, R^4, R^6, R^7, R^8, R^9$ and $R^{10}$ are the same or different and represent a hydrogen atom or a group selected between —OCH$_3$ or —OH.

A more preferred embodiment of the invention described herein entails a general formula (IV) compound selected, but without limitation, from among the following group: 2-(2,5-dihydroxyphenyl)-1H-indole-4,6-diol; 4,6-Dimethoxy-2-(3,5-dimethoxyphenyl)-1H-indole; 4,6-Dimethoxy-2-(2,5-dimethoxyphenyl)-1H-indole-1-tert-butyl carboxylate; 4,6-Dimethoxy-2-(2,5-dimethoxyphenyl)-1H-indole; and 4,6-Dimethoxy-2-(3,5-dimethoxyphenyl)-1H-indole-1-tert-butyl carboxylate.

The term "analogs" means, in this description, compounds of a similar structure, in other words, is bearing a similarity on the periphera of said molecules.

Figure 1:
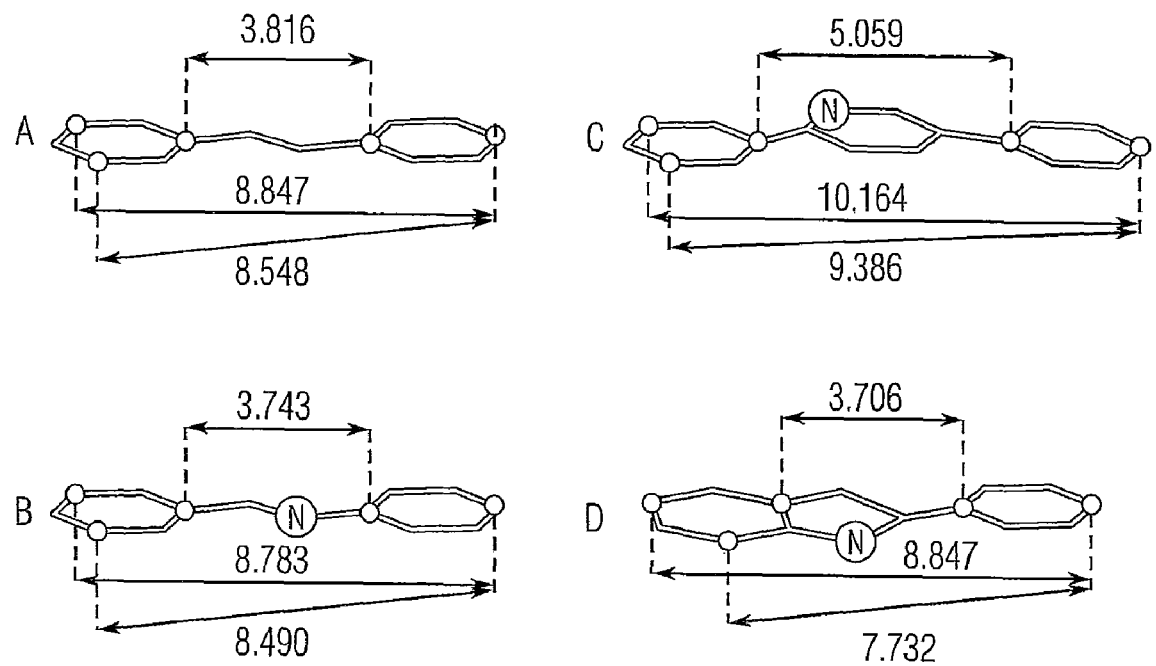
FIG. 1.—Shows the optimized structures, calculated using the MP3 method (cf. Stewart, J. *Comput. Chem.* 1989, vol. 10 pp. 209), of (A) trans-stilbene; (B) diphenylmine; (C) 2,4-diphenyl-1H-pyrol; y (D) 2 phenyl-1H-indole.

As is shown in FIG. 1, in the substituted trans-stilbenes, the distances between the quaternary aromatic atoms which bond the phenyl groups to the central group are on the order of 3.82 Å, a value within a mid-range as compared to that calculated for N-benzylidene anilines 1 (ca. 3.74 Å, FIG. 1B), 2,4-diaryl-1H-pyrroles (ca. 5.06 Å, FIG. 1C) and 2-aryl-1H-indoles (each 3.71 Å, FIG. 1D). Likewise, some hypothetical hydroxyl or alkoxy groups in a relative arrangement similar to that of the trans-resveratrol are spaced at the intervals of 10.16-8.78 Å and 9.39-7.73 Å for compounds I, II and III, values which encompass those of the resveratrol proper (8.85 Å and 8.55 Å respectively, FIG. 1A). Therefore, the compounds of the invention make it possible to extend the therapeutical applications of the Trans-stilbenes on broadening the geometric parameters of the pharmacophore and to provide the possibility of optimizing interactions of major importance for the desired pharmacological activity.

The compounds described are of the following structural formula:

5-((E)-(4-Hydroxyphenylimino)methyl)benzene-1,3-diol, referred to hereinafter as "Azaresveratrol":

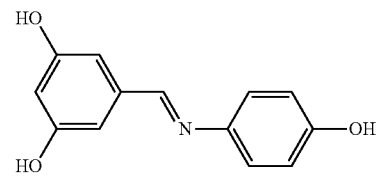

3,5-bis(3,5-Dihydroxyphenyl)-1H-pyrrole-2-methyl carboxylate, referred to hereinafter as "JE2:2":

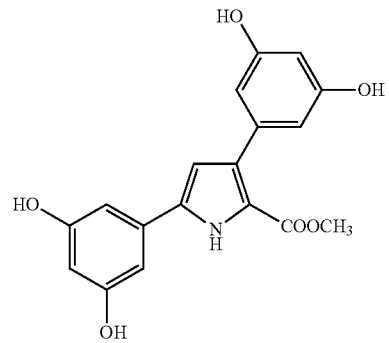

3,5-bis(3,5-Dimethoxyphenyl)-1H-pyrrole-2-methyl carboxylate, referred to hereinafter as "JEM2:2-01":

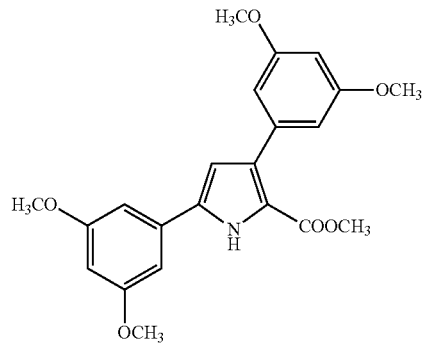

5-(3,5-Dihydroxyphenyl)-3-(4-hydroxyphenyl)-1H-pyrrole-2-methyl carboxylate, referred to hereinafter as "JE2:1":

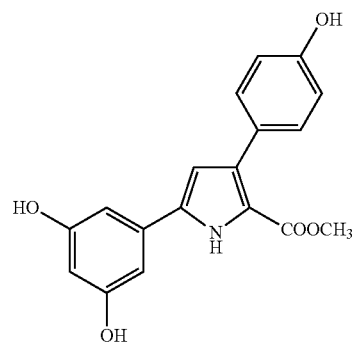

5-(3,5-dimethoxyphenyl)-3-(4-methoxyphenyl)-1H-pyrrole-2-methyl carboxylate:

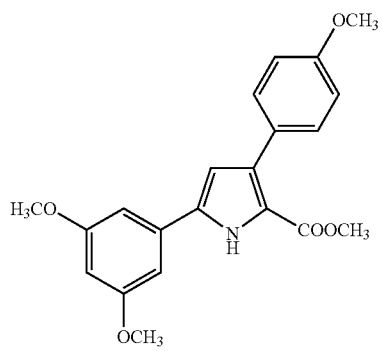

3-(3,5-Dihydroxyphenyl)-5-(4-hydroxyphenyl)-1H-pyrrole-2-methyl carboxylate, referred to hereinafter as "JE1:2":

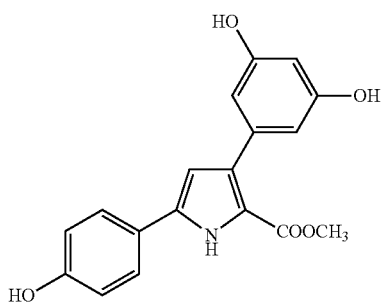

5-(3,5-dimethoxyphenyl)-3-(4-methoxyphenyl)-1H-pyrrole-2-methyl carboxylate:

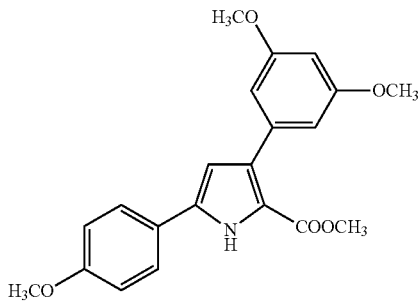

3,5 acid 3,5-bis(3,5-dimethoxyphenyl)-1H-pyrrole-2-carboxylic acid:

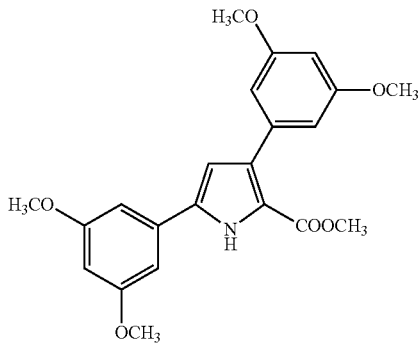

3-(4-methoxyphenyl)-5-(dimethoxyphenyl)-1H-pyrrole-2-carboxylic acid, referred to hereinafter as "JEM2: 1-02":

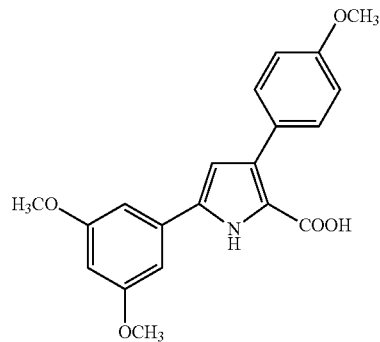

5-(3,5-dimethoxyphenyl)-3-(4-methoxyphenyl)-4-nitro-1H-pyrrole-2-carboxylate:

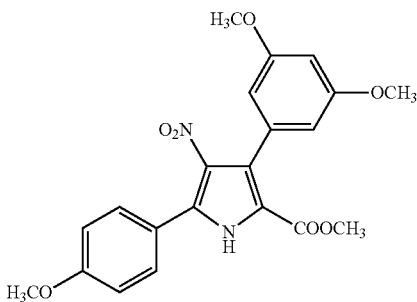

3,5 acid 3,5-bis(3,5-dimethoxyphenyl)-1H-pyrrole-2-methyl carboxylate:

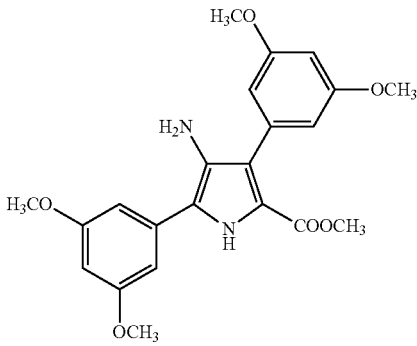

5-(3,5-dimethoxyphenyl)-3-(4-methoxyphenyl)-4-nitro-1H-pyrrole-2-methyl carboxylate:

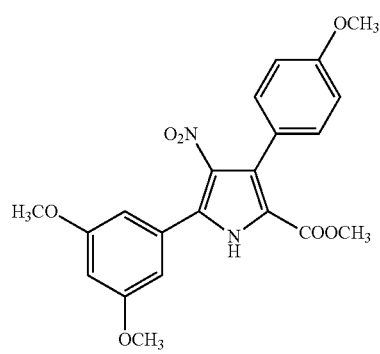

3,5-bis(3,5-dimethoxyphenyl)-4-nitro-1H-pyrrole-2-methyl carboxylate:

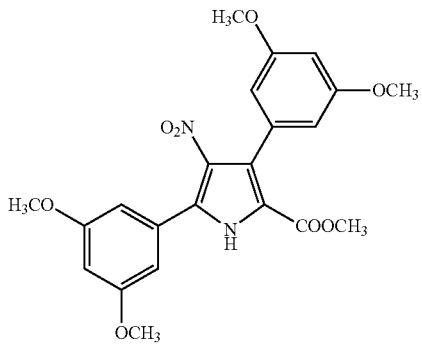

2-(2,5-Dihydroxyphenyl)-1H-indole-4,6-diol, referred to hereinafter as "YEF05H":

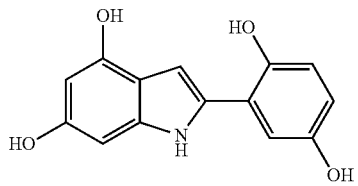

4,6-Dimethoxy-2-(3,5-dimethoxyphenyl)-1H-indole, referred to hereinafter as "YEF07":

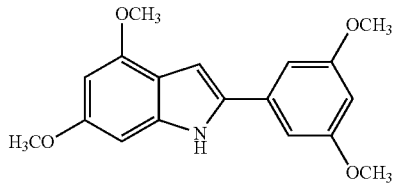

4,6-Dimethoxy-2-(2,5-dimethoxyphenyl)-1H-indole:

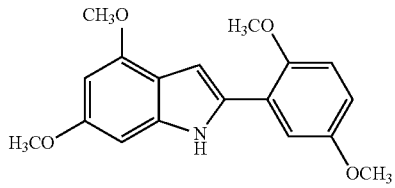

4,6-Dimethoxy-2-(2,5-dimethoxyphenyl)-1H-indole-1-tert-butyl carboxylate, referred to hereinafter as "YEF07B":

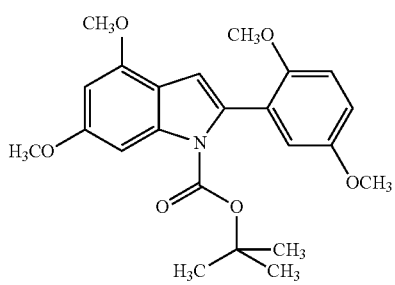

4,6-Dimethoxy-2-(3,5-dimethoxyphenyl)-1H-indole-1-tert-butyl carboxylate, referred to hereinafter as "YEF05B":

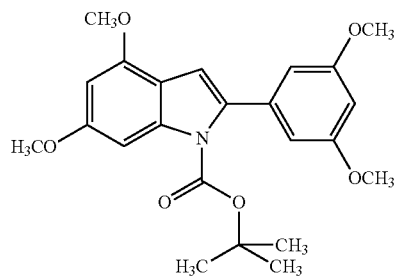

A second aspect of the invention described herein is the method for obtaining the general formula (II) compound, which entails reacting in the presence or absence of an organic solvent:

i) an aromatic aldehyde suitably substituted for alkoxy or hydroxyl groups of the following formula (V),

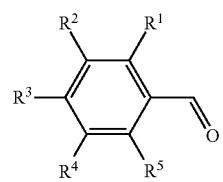

(V)

wherein:

$R^1$, $R^2$, $R^3$, $R^4$ and $R^5$ are of the same meaning as previously stated hereinabove;

ii) an aniline of formula (VI) similarly substituted

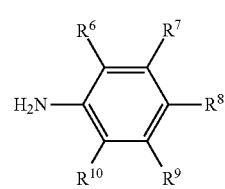

(VI)

wherein:

$R^6$, $R^7$, $R^8$, $R^9$ and $R^{10}$ are of the same meaning as previously stated hereinabove.

A preferred embodiment of the method for obtaining the formula (II) compound employs a drying agent selected, without limitation, between either a suitable anhydrous salt or molecular sieve.

After eliminating the solvent and the drying agent, in the event that either one thereof is used, the resulting reaction mixture is purified by means of crystallization in the suitable solvent known by any expert on the subject.

A third aspect of the invention described herein provides a method for obtaining the formula (III) compound which entails reacting:

i) an (E) or (Z)-configuration imine of the following formula (VII):

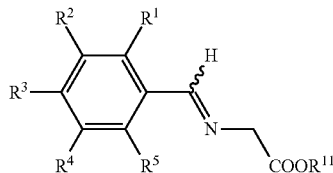

(VII)

wherein:

$R^1$, $R^2$, $R^3$, $R^4$ and $R^5$ are of the same meaning as previously stated hereinabove, and $R^{11}$ represents an alkyl ($C_1$-$C_{10}$), preferably methyl, an aryl or an heteroaryl group;

ii) an (E) or (Z)-configuration nitroalkene of the formula (VIII):

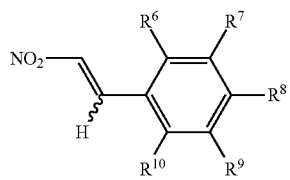

(VIII)

where:

$R^6$, $R^7$, $R^8$, $R^9$ and $R^{10}$ are of the same meaning as previously stated hereinabove;

iii) a metallic salt, selected, without limitation, from among lithium perchlorate, silver perchlorate or silver acetate; and iv) a tertiary organic base selected from among the aliphatic bases with $C_3$-$C_{10}$ carbons or alkane-aromatic bases with $C_9$-$C_{15}$ carbons.

The reaction mixture can be made by means of microwave radiation or by adding one of the components to the other three, in an organic solvent and at the temperature of −25° C. to +25° C., preferably at temperatures nearing +25° C.

The completion of the cycloaddition reaction results in obtaining a mixture of 2-alkoxycarbonil pyrroleidines corresponding to the substitutes selected for each individual reaction. Said mixture is dissolved in a cyclic ether such as high-boiling-point acyclic or tetra-hydrofurane such as diethylene glycol dimethyl ether, also known as "diglyme" and an oxidizing agent added such as manganese dioxide, hydrogen peroxide or 2,3-dichloride-5,6-dicyano-1,4-benzoquinone. After a certain length of time at temperatures ranging from +60° C. to +250° C., the corresponding mixture is obtained comprised of 2-alkoxycarbonyl-NH-pyrrole (IX) and 2-alkoxycarbonyl-4-nitro-NH-pyrrole (X) the components of which can be separated by means of fractioned crystallization or chromatography:

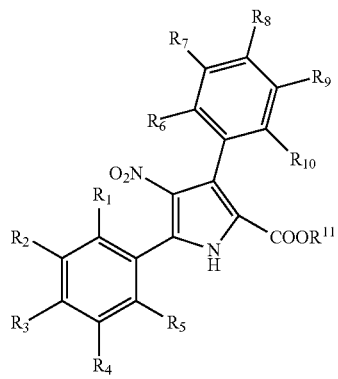

(IX)

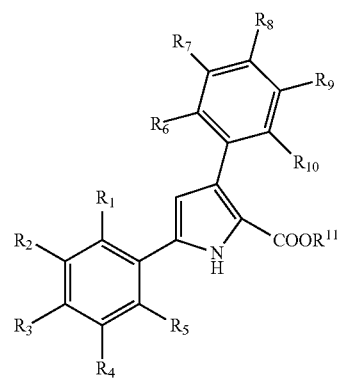

(X)

These (IX and X) compounds pertain to the family of compounds of general formula (III) included in the invention described herein, in the particular cases in which (Y) is $NO_2$ or (W) is $COOR^{11}$; (Z) is H and $R^1$-$R^{10}$ may be the same or different and are selected from among a hydrogen atom or a group selected between either alkoxy (—OR) or hydroxyl (—OH), where at least three of these substitutes are either alkoxy and/or hydroxyl;

For all of the other cases, the starting compounds are (IX) and (X), and the following chemical transformations are carried out:

To obtain the general formula (III) compounds, wherein (Y) is $NH_2$ and the derivatives thereof, the nitro group is reduced to the amine group preferably by reacting the corresponding nitrocompound with tin dichloride at temperatures ranging from +25° C. to +90° C. Following the purification of the corresponding primary amine, this amine may be transformed into derivatives of the substituted amine, amide or ammonium salt type by means of conventional processes.

To obtain the formula (III) compounds wherein (W) is COOH, the hydrolysis of the ester function present in the compounds (IX) and (X) is preferably achieved by means of the treatment thereof with sodium or lithium hydroxide in a mixture of water and dimethoxyethane.

To obtain the formula (III) compounds wherein (W) is H, the decarboxylation of the carboxylic acids obtained in the preceding paragraph hereinabove is preferably achieved by means of thermolysis at pressures ranging from 5 mm Hg to 0.01 mm Hg and at temperatures ranging from +150° C. and +250° C.

To obtain the compounds of formula (III) wherein $R^1$-$R^{10}$ are OH, the transformation of the methoxyl group into hydroxyl groups is preferably achieved by reacting the corresponding methoxylate compound under an inert atmosphere preferably of argon, with a solution of boron tribromide in dichloromethane at temperatures ranging from −20° C. to +30° C. for 2-24 hours, following which the mixture is treated with methanol at 0° C.

To obtain the formula (III) compound where (Z) may be alkyl ($C_1$-$C_{10}$), aryl, O-alkyl(aryl)carbamoyl or N-alkyl (aryl)-semicarbazide. The substitution of the carbon atom present in the (IX) and (X) compounds is achieved by means of conventional alkylation and acylation methods. In the cases in which inertia is observed in the acylation, this may be facilitated by means of the use of anhydrides a catalyst acylating agents, preferably 4-dimethylaminopyridine and zinc perchlorate.

A fourth aspect of the invention described herein provides a method for obtaining the formula (VI) compound, which entails reacting:

i) an amine of formula (XI) below,

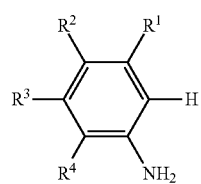

wherein:
$R^1$, $R^2$, $R^3$ and $R^4$ are of the same meaning as previously stated hereinabove;

ii) an alpha-halocetone of formula (XII) below,

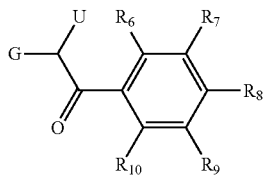

wherein:
(G) may be a halogen selected from chlorine, bromine and iodine;
(U) is of the same meaning as previously stated hereinabove, and
$R^6$, $R^7$, $R^8$, $R^9$ and $R^{10}$ are of the same meaning as previously stated hereinabove;

iii) a tertiary amine such as N,N-dimethylaniline or any combination of aryl, heteroaryl or linear, cyclic or branched alkyl groups.

For the purposes of the invention described herein, the reaction mixture comprised of the three immediately preceding components stated hereinabove can be achieved by means of microwave radiation in the absence of a solvent at a temperature ranging from +90° C. to +180° C., preferably at temperatures nearing +150° C., with a radiation power of 25 to 200 W, preferably employing radiation power nearing 100 W, for radiation times of 5 to 30 minutes, the preferred radiation times being of around 10 minutes. The radiation may be taken to atmospheric pressure or to pressures of 50 to 200 psi (Pounds/square inch). Upon completion of the reaction, general formula (XIII) 2-aryl-1H-indoles are obtained.

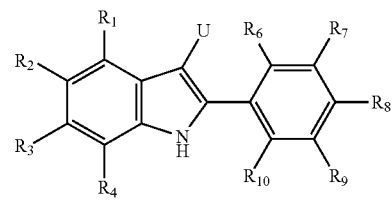

Said (XIII) compounds pertain to the general formula (IV) compounds included in the invention described herein, in the particular cases in which (Z) is H and $R^1$-$R^{10}$ are of the same meaning as previously stated hereinabove.

For all of the other cases, starting from the (XIII) compounds, the following transformations are carried out:

To obtain the formula (IV) compound wherein any of the $R^1$-$R^{10}$ groups are OH, the transformation of the methoxyl groups into hydroxyl groups is preferably achieved by reacting the corresponding methoxylated compound under an inert atmosphere preferably of argon, with a solution of boron tribromide in dichloromethane at temperatures ranging from −20° C. to +30° C. for 2-24 hours, following which the mixture is treated with methanol at 0° C.

To obtain the formula (IV) compound wherein (Z) can be alkyl ($C_1$-$C_{10}$), aryl, O-alkyl(aryl)carbamoyl or N-alkyl (aryl)-semicarbazide: the substitution of the hydrogen atom present in the XIII compounds is achieved by means of conventional alkylation and acylation methods. In those cases in which inertia is observed in the acylation, the acylation can be facilitated by means of employing anhydrides as catalyst acylating agents, preferably 4-dimethylaminopyridine and zinc perchlorate.

A fifth aspect of the present invention provides the use of the general formula (I) compounds for the treatment or chemoprevention of those mammalian diseases such as cancer, fibrosclerosis and acute/chronic inflammation, graft-versus-host reaction, ischemic-reperfusion tissue injury in stroke and heart attack, neurodegeneration, and during organ transplantation, whose pathogenic and pathophysiological mechanisms depend on or are significantly contributed by undesirable oxidative stress, angiogenic and proliferative responses.

A sixth aspect of the invention provides the use of any of the general formula (I) compounds or combinations thereof for the preparation of a pharmaceutically-acceptable composition for the treatment and prophylaxis of diseases involving cancerigenous and inflammatory processes, more preferably, but without limitation to, the treatment of hepatic metastasis.

One embodiment of the preparation of a composition may be, without being limited to, that of a composition which includes at least one of the general formula (II) compounds and one or more pharmaceutically-acceptable excipients. A composition may likewise be prepared for the formula (III) and (IV) compounds. The formula (II), (III) and (IV) compounds of the invention described herein may be administered both as a pure substance as well as in the form of pharmaceutical formulations, although the administration of the combined-form composition is preferable.

Another aspect of the invention described herein provides a pharmaceutical composition which includes:
i) at least one general formula (I) compound, preferably general formula (II), (III) or (IV), or any combination thereof:
ii) pharmaceutically-acceptable vehicles; and
iii) additionally, a therapeutically-active substance The term "pharmaceutically-acceptable vehicle" is understood as employed in the invention described herein as one or more excipients and/or carrier substances or auxiliary substances which are pharmaceutically or pharmacological tolerable, such that they may be combined with other components in the formulation or preparation and will have no adverse effects on the organism treated.

The term "therapeutically-active substance" is understood as employed in the invention described herein, as any substance synergistically interacting with resveratrol, such as, but not limited to, other polyphenols such as quercetin.

The pharmaceutical compositions include, but are not limited to, those which are suitable for oral or parenteral (including subcutaneous, intradermic, intramuscular and intravenous) administration, although the best way of administering depends upon the patient's condition.

The formulations may be in single-dose form and be prepared in accordance with methods known by any expert on the subject in the field of pharmacology. The quantities of active substances to be administered may vary in terms of the individual aspects of the therapy.

The following examples and figures provided in following serve to illustrate yet not limit the invention described herein.

EXAMPLES OF EMBODIMENT

Example 1

Preparation of 5-((E)-(4-Hydroxyphenylimine)methyl)benzene-1,3-diol, of the following structural formula

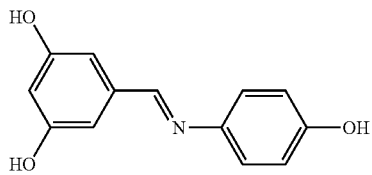

Anhydrous magnesium sulfate was added to a suspension of dry dichloromethane (5 ml) of 4-aminophenol (0.109 g, 1 mmol) and of 3,5 dihydroxybenzaldehyde (0.138 g, 1 mmol). The resulting mixture was agitated at ambient temperature for 3 hours. In following, the solvent was evaporated a low pressure and ethanol (5 mL) is added to the resulting residue. The mixture was heating to boiling and then filtered. The filtrate was evaporated under low pressure to yield a residue which was ground to a minimal quantity of cold ethanol, thus yielding 5-((E)-(4-Hydroxyphenylimine)methyl)benzene-1,3-diol. Yield: 100%; p. f. (° C.) 162 (desc.).); IR (KBr) 3494, 3287, 1631, 1598, 1508, 1461, 1339, 1273, 1155 cm$^{-1}$; $^1$H NMR (300 MHz, DMSO-d$_6$) δ 9.44 (s, 1H), 9.42 (s, 2H), 8.38 (s, 1H), 7.15 (d, J=7.8 Hz, 2H), $^{13}$C NMR (63 MHz, DMSO-d$_6$) δ 158.6, 157.4, 156.2, 142.6, 138.4, 122.5, 115.7, 106.4, 105.3. Calc. Analysis for $C_{13}H_{11}NO_3$: C, 68.11; H, 4.84; N, 6.11. Found: C, 68.76; H, 4.92; N, 6.21%.

Example 2

Preparation of 3,5-bis(3,5-dimethoxyphenyl)-1H-pyrrole-2-methyl carboxylate, of the following structural formula

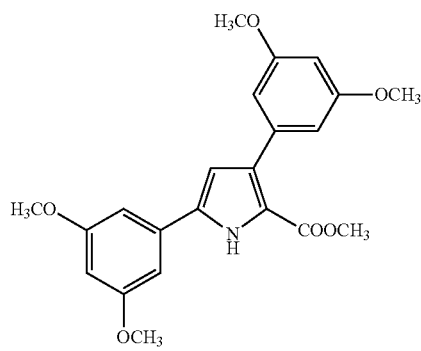

and of 3,5-bis(3,5-dimethoxyphenyl)-4-nitro-1H-pyrrole-2-methyl carboxylate, of the following structural formula:

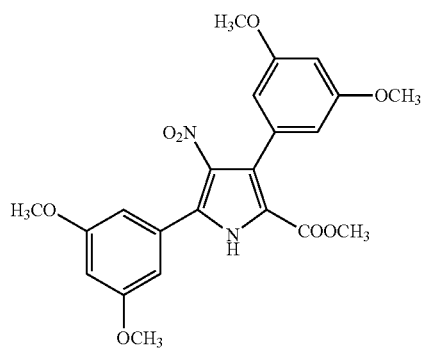

In a spherical flask, (3,5-dimethoxybenzyllidenamine)methyl acetate (2.0 g, 8.4 mmoles) was dissolved in 84 ml of CH$_3$CN, then adding 1.2 ml (1.25 mmoles) detriethyllamine, 1,3-dimethoxy-5-(2-nitrovinyl)benzene (1.8 g, 8.4 mmoles) and 0.21 g (1.25 mmoles) of AgOAc. The progress of the reaction was monitored by means of thin-layer chromatography. Following completion of the reaction (approx. 5 hours), the mixture was filtered through a celite bed and the filtrate washed with an aqueous NH$_4$Cl solution (2×84 ml) and H$_2$O (2×84 ml), was then dried on anhydrous Na$_2$SO$_4$ and evaporated at low pressure. The crude portion was purified by means of pressurized chromatography column (AcOEt/Hx). 1.8 g (4 mmoles) of the oil obtained was dissolved in 40 ml of 2-methoxyethylether under argon atmosphere. In following, 3.5 g (40 mmoles) MnO$_2$ were added and agitated to reflux for 48 hours. The reaction mixture was filtered through celite and the filtrate evaporated at low pressure. The products were separated by means of flash column chromatography, obtaining 3,5-bis(3,5-dimethoxyphenyl)-1H-pyrrole-2-methyl carboxylate and 3,5-bis(3,5-dimethoxyphenyl)-4-nitro-1H-pyrrole-2-methyl carboxylate.

3,5-bis(3,5-dimethoxyphenyl)-4-nitro-1H-pyrrole-2-methyl carboxylate: Yield. 25%; p.f. 139-141° C.; IR 3447, 3246, 1698, 1592, 1507, 1211, 1161 cm$^1$; $^1$H-RMN (δ ppm, CDCl$_3$) 9.42 (s, 1H), 6.70 (d, 2H, J=2.3 Hz), 6.56 (t, 1H, J=82.2 Hz), 6.50 (s, 3H), 3.82 (s, 6H), 3.69 (s, 3H); $^{13}$C-RMN (δ ppm, CDCl₃) 161.3, 161.1, 160.5, 134.1, 133.9, 133.1, 130.6, 124.4, 118.4, 108.3, 107.2, 102.6, 100.7, 55.9, 55.7, 52.5. Calc. Analysis for C₂₂H₂₂N₂O₈: C, 59.73; H, 5.02; N, 6.33. Found: C, 59.41; H, 4.73; N, 6.36%. 3,5-bis(3,5-dimethoxyphenyl)-1H-pyrrole-2-methyl carboxylate: Yield: 31% p.f. 113-115° C.; IR 3276, 1668, 1608, 1156 cm⁻¹; ¹H-RMN (δ ppm, CDCl₃) 9.28 (s, 1H), 6.77 (d, 2H, J=2.3 Hz), 6.71 (d, 2H, J=2.2 Hz), 6.60 (d, 2H, J=3.1 Hz), 6.60 (d, 2H, J=3.1 Hz), 6.46 (t, 1H, J=2.3 Hz), 6.44 (t, 1H, J=2.2 Hz), 3.84 (s, 6H), 3.82 (s, 3H); ¹³C-RMN (δ ppm, CDCl₃) 161.9, 161.7, 160.5, 137.1, 135.7, 133.5, 133.1, 118.6, 110.6, 107.9, 103.4, 100.4, 100.0, 55.9, 55.7, 51.9. Calc. Analysis for C₂₂H₂₃N₂O₆: C. 66.49; H. 5.84; N. 3.52. Found: C. 66.13; H. 5.47; N, 3.66%.

Example 3

Preparation of 5-(3,5-dimethoxyphenyl)-3-(4-methoxyphenyl)-1H-pyrrole-2-methyl carboxylate, of the following structural formula

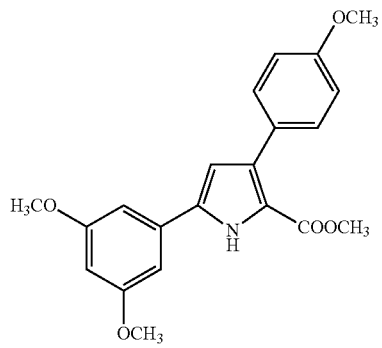

and of 5-(3,5-dimethoxyphenyl)-3-(4-methoxyphenyl)-4-nitro-1H-pyrrole-2-methyl carboxylate, of the following structural formula:

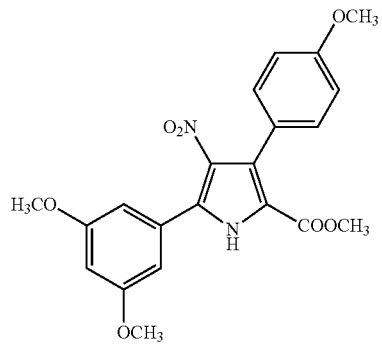

Both compounds were prepared and separated by means of a procedure similar to that described in Example 2 hereinabove.

5-(3,5-dimethoxyphenyl)-3-(4-methoxyphenyl)-4-nitro-1H-pyrrole-2-methyl carboxylate: Yield: 20%; p.f 194-145° C.; IR 3266, 1683, 1597, 1507, 1276, 1211, 1166 cm⁻¹; ¹H-RMN (δ ppm. CDCl₃) 9.42 (s. 1H). 7.32 (d. 2H. J=8.3 Hz). 6.96 (d. 2H. J=8.3 Hz). 6.71 (s. 2H). 6.58 (s. 1H). 3.87 (s. 3H). 3.84 (s. 3H). 3.71 (s. 3H), ¹³C-RMN (δ ppm. CDCl₃) 161.4, 161.2, 159.7, 134.4, 133.9, 131.4, 130.6, 127.6, 123.2, 118.3, 113.5, 107.2, 103.5, 102.4, 55.9, 55.5, 52.4. Calc. Analysis for C₂₁H₂₀N₂O₇: C. 61.16; H. 4.90; N. 6.80. Found: C. 61.47; H. 4.92; N. 7.00%.

5-(3,5-dimethoxyphenyl)-3-(4-methoxyphenyl)-1H-pyrrole-2-methyl carboxylate: Yield: 35%; p.f. 123-125° C.; IR 3286, 1678, 1211 cm⁻¹; ¹H-RMN (δ ppm, CDCl₃) 9.24 (s, 1H), 7.55 (d, 2H, J=8.6 Hz), 6.95 (d, 2H, J=8.6 Hz), 6.72 (s, 2H), 6.58 (d, 2H, J=2.9 Hz), 6.45 (s, 1H), 3.86 (s, 9H), 3.82 (s, 3H); ¹³C-RMN (δ ppm, CDCl₃) 161.9, 161.7, 159.2, 135.7, 133.7, 133.3, 130.8, 127.7, 118.2, 113.6, 110.4, 103.5, 100.3, 55.8, 55.6, 51.7. Calc. Analysis for C₂₁H₂₁NO₅: C, 68.65: H, 5.77; N, 3.81. Found: C, 68.35; H, 6.00; N, 3.95%.

Example 4

Preparation of 5-(3,5-dimethoxyphenyl)-3-(4-methoxyphenyl)-1H-pyrrole-2-methyl carboxylate, of the following structural formula

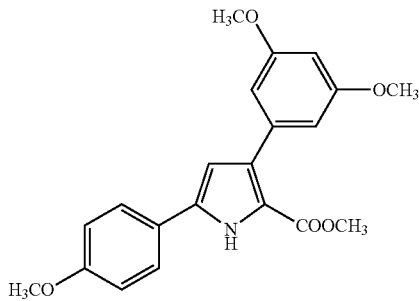

and of 5-(3,5-dimethoxyphenyl)-3-(4-methoxyphenyl)-4-nitro-1H-pyrrole-2-methyl carboxylate, of the following structural formula:

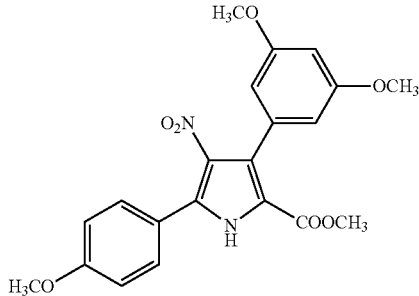

Both compounds were prepared and separated by means of a procedure similar to that described in Example 2.

3-(3,5-dimethoxyphenyl)-5-(4-methoxyphenyl)-4-nitro-1H-pyrrole-2-methyl carboxylate: Yield: 20%; p.f. 176-178° C.; IR 3286, 1683, 1618, 1507, 1311 cm⁻¹; ¹H-RMN (δ ppm, CDCl₃) 9.20 (s, 1H), 7.56 (d, 2H, J=8.7 Hz), 7.02 (d, 2H, J=8.7 Hz), 6.52 (s, 3H), 3.89 (s, 3H), 3.82 (s, 6H), 3.74 (s, 3H); ¹³C-RMN (δ ppm, CDCl₃) 161.1, 160.2, 134.7, 133.2, 130.5, 127.4, 120.9, 118.0, 114.4, 108.1, 100.4, 100.3, 55.6, 55.5, 52.2. Calc. Analysis for C₂₁H₂₀N₂O₇: C, 61.16; H, 4.90; N, 6.80. Found: C, 61.20; H, 5.15; N, 6.87%.

3-(3,5-dimethoxyphenyl)-5-(4-methoxyphenyl)-1H-pyrrole-2-methyl carboxylate: Yield: 28%; p.f. 149-150° C.; IR 3326, 1673, 1151 cm⁻¹; ¹H-RMN (δ ppm, CDCl₃) 9.18 (s, 1H), 7.51 (d, 2H, J=8.7 Hz), 6.96 (d, 2H, J=8.7 Hz), 6.77 (d, 2H, J=2.5 Hz), 6.53 (d, 2H, J=2.5 Hz), 6.45 (s, 1H), 3.84 (s, 3H), 3.82 (s, 6H), 3.80 (s, 3H); ¹³C-RMN (δ ppm, CDCl₃) 161.8, 160.3, 159.7, 135.1, 135.8, 133.5, 126.3, 123.9, 117.8, 114.6, 109.3, 107.7, 99.8, 55.5, 51.5. Calc. Analysis for C$_{21}$H$_{21}$NO$_5$: C, 68.65; H, 5.77; N, 3.81. Found: C, 68.52; H, 5.42; N, 4.08%.

Example 5

Preparation of 3,5-bis(3,5-Dihydroxyphenyl)-1H-pyrrole-2-methyl carboxylate, of the following structural formula

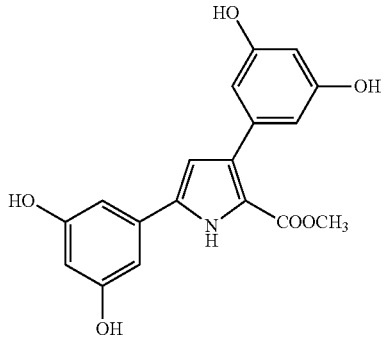

In a spherical flask cooled to 0° C. and under argon atmosphere, 0.2 g (0.5 mmoles) of 3,5-bis(3,5-Dimethoxyphenyl)-1H-pyrrole-2-methyl carboxylate (Prepared as stated in Example 2) were dissolved in 12 ml of dry dichloromethane. In following, 6 ml of BBr$_3$ (1 M in dichloromethane) were added drop by drop and agitated to ambient temperature for 16 hours. The reaction was halted by adding MeOH at 0° C. drop by drop. The resulting solid was filtered and purified by means of pressurized column chromatography. (Eluent: MeOH/CH$_2$Cl$_2$) obtaining the compound 3,5-bis(3,5-hydroxyphenyl)-1H-pyrrole-2-methyl carboxylate.

3,5-bis(3,5-hydroxyphenyl)-1H-pyrrole-2-methyl carboxylate: Yield: 69% p.f. 233-235° C.; IR 3427, 1618 cm$^{-1}$; $^1$H-RMN (δ ppm, DMSO-d$_6$) 11.2 (s, 1H), 9.20 (s, 2H), 9.03 (s, 2H), 7.04 (s, 1H), 6.52 (s, 1H), 6.48 (s, 2H), 6.40 (s, 2H), 6.09 (s, 1H), 6.02 (s, 1H); $^{13}$C-RMN (δ ppm, DMSO-d$_6$) 161.0, 157.7, 157.2, 137.2, 136.3, 133.4, 127.1, 122.4, 117.1, 115.6, 108.5, 107.7, 101.3, 51.0. Calc. Analysis for C$_{18}$H$_{15}$NO$_6$: C, 66.46; H, 4.65; N, 4.31. Found: C, 66.13; H, 4.57; N, 4.36%.

Example 6

Preparation of 5-(3,5-Dihydroxyphenyl)-3-(4-hydroxyphenyl)-1H-pyrrole-2-methyl carboxylate, of the following structural formula

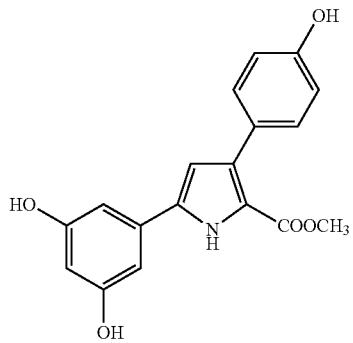

This compound was prepared and purified according to a procedure similar to that described in Example 5.

5-(3,5-Dihydroxyphenyl)-3-(4-hydroxyphenyl)-1H-pyrrole-2-methyl carboxylate: Yield: 63%; p.f. breaks down; IR 3537, 3397, 3316, 1673, 1597, 1271, 1161 cm$^{-1}$; $^1$H-RMN (δ ppm, DMSO-d$_6$) 11.6 (s, 1H), 9.41 (s, 1H), 9.34 (s, 2H), 7.34 (d, 2H, J=8.5 Hz), 6.74 (d, 2H, J=8.5 Hz), 6.67 (d, 2H, J=2.1 Hz), 6.46 (d, 2H, J=2.1 Hz), 6.19 (s, 1H), 3.68 (s, 3H); $^{13}$C-RMN (δ ppm, DMSO-d$_6$) 161.0, 158.6, 156.5, 136.2, 132.9, 130.4, 126.0, 117.4, 114.6, 109.4, 104.0, 102.2, 50.9. Calc. Analysis for C$_{18}$H$_{15}$NO$_5$: C, 66.46; H, 4.65; N, 4.31. Found: C, 66.60; H, 4.41; N, 4.26%.

Example 7

Preparation of 3-(3,5-Dihydroxyphenyl)-5-(4-hydroxyphenyl)-1H-pyrrole-2-methyl carboxylate, of the following structural formula

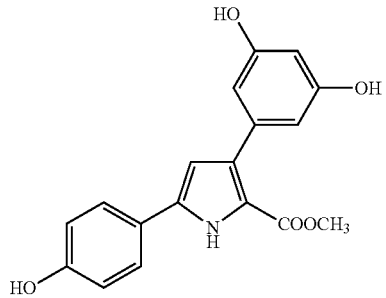

This compound was prepared and purified according to a procedure similar to that described in Example 5.

3-(3,5-Dihydroxyphenyl)-5-(4-hydroxyphenyl)-1H-pyrrole-2-methyl carboxylate: Yield: 66%; p.f. 234-236° C.; IR 3326, 1678, 1608, 1281, 1161 cm$^{-1}$; $^1$H-RMN (δ ppm, DMSO-d$_6$) 11.6 (s, 1H), 9.64 (s, 1H), 9.16 (s, 2H), 7.66 (d, 2H, J=8.6 Hz), 6.78 (d, 2H, J=8.6 Hz), 6.45 (d, 2H, J=2.3 Hz), 6.37 (d, 2H, J=2.3 Hz), 6.19 (s, 1H), 3.69 (s, 3H); $^{13}$C-RMN (δ ppm, DMSO-d$_6$) 161.0, 157.7, 157.2, 137.2, 136.3, 133.4, 127.1, 122.4, 117.1, 115.6, 108.5, 107.7, 101.3, 51.0. Calc. Analysis for C$_{18}$H$_{15}$NO$_5$: C, 66.46; H, 4.65; N, 4.31. Found: C, 66.67; H, 4.61; N, 4.23%.

Example 8

Preparation of 3,5-bis(3,dimethoxyphenyl)-1H-pyrrole-2-carboxylic acid, of the following structural formula

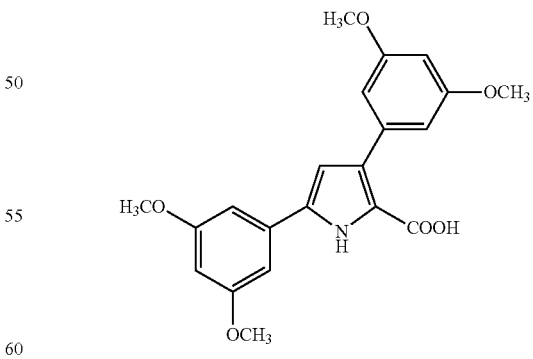

In a spherical flask, 0.45 g (1.1 mmoles) of 3,5-bis(3,5-dimethoxyphenyl)-1H-pyrrole-2-methyl carboxylate (Prepared as stated in Example 2), 11 ml of 10% and 28 ml of ethanol were agitated for 3 hours to reflux. After cooling the reaction flask, the reaction crude was neutralized with HCl 1 M.

In following, the ethanol was evaporated at low pressure and the resulting aqueous phase was washed with AcOEt. Lastly, the organic phase was dried on $Na_2SO_4$ and was evaporated at low pressure, obtaining the compound 3,5-bis (3,5-dihydroxyphenyl)-1H-pyrrole-2-carboxylic acid.

3,5-bis(3,5-dimethoxyphenyl)-1H-pyrrole-2-carboxylic acid: Yield: 98%; p.f. 169-171° C.; IR 3316, 1653, 1608, 1196, 1156 cm$^{-1}$; $^1$H-RMN (δ ppm, CDCl$_3$) 11.0 (s, 1H), 9.37 (s, 1H), 6.80 (d, 2H, J=2.0 Hz), 6.74 (d, 2H, J=2.0 Hz), 6.65 (d, 2H, J=2.8 Hz), 6.52-6.43 (m, 2H), 3.86 (s, 6H), 3.84 (s, 6H); $^{13}$C-RMN (δ ppm, CDCl$_3$) 165.0, 161.6, 160.5, 136.7, 136.5, 135.1, 132.7, 117.5, 110.9, 107.8, 103.5, 100.6, 100.2, 55.7, 55.6. Calc. Analysis for $C_{21}H_{21}NO_6$: C, 65.79; H, 5.52; N, 3.65. Found: C, 65.71; H, 5.27; N, 3.55%.

Example 9

Preparation of 3-(4-methoxyphenyl)-5-(dimethoxyphenyl)-1H-pyrrole-2-carboxylic acid, of the following structural formula

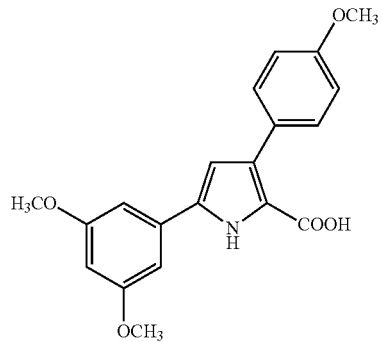

This compound was prepared and purified according to a procedure similar to that described in Example 8.

3-(4-methoxyphenyl)-5-(dimethoxyphenyl)-1H-pyrrole-2-carboxylic acid: Yield: 85%; p.f. 152-153° C.; IR 3475, 3306, 1648, 1597, 1251, 1211, 1156 cm$^{-1}$; $^1$H NMR (δ ppm, CDCl$_3$) 11.3 (s, 1H), 9.30 (s, 1H), 7.56 (d, 2H, J=8.5 Hz), 6.94 (d, 2H, J=8.5 Hz), 6.72 (d, 2H, J=1.7 Hz), 6.60 (d, 1H, J=2.6 Hz), 6.46 (s, 1H), 3.85 (s, 9H); $^{13}$C NMR (δ ppm, CDCl$_3$) 161.2, 158.7, 137.9, 133.2, 126.7, 125.7, 125.5, 115.3, 114.6, 103.7, 103.3, 99.1, 55.5. Calc. Analysis for $C_{20}H_{19}NO_5$: C, 67.98; H, 5.42; N, 3.96. Found: C, 67.88; H, 5.51; N, 4.00;

Example 10

Preparation of 2,4-bis(3,5-dihydroxyphenyl)-1H-pyrrole, of the following structural formula

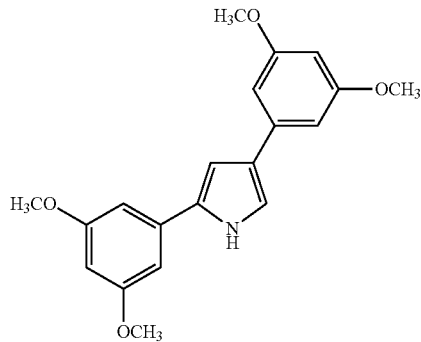

0.1 g (0.26 mmoles) of the 3,5-bis(3,5-dimethoxyphenyl)-1H-pyrrole-2-carboxylic acid (Prepared as stated in Example 8) were heated for 1 hour to 180-200° C. at a pressure of 1.2 mmHg. Upon completion of the reaction, the crude was cooled, obtaining 2,4-bis(3,5-dihydroxyphenyl)-1H-pyrrole, which was purified by means of column chromatography (Eluent: AcOEt/hexanes).

3,5-bis(3,5-Dimethoxyphenyl)-1H-pyrrole: Yield: 92%; p.f. 124-125° C.: IR 3427, 1597, 1212, 1161 cm$^{-1}$; $^1$H-RMN (δ ppm, CDCl$_3$) 8.43 (s, 1H), 7.08 (s, 1H), 6.75 (s, 1H), 6.70 (d, 2H, J=2.2 Hz), 6.63 (d, 2H, J=2.1 Hz), 6.35 (t, 1H, J=2.1 Hz), 6.33 (t, 1H, J=2.2 Hz), 3.82 (s, 12H); $^{13}$C-RMN (δ ppm, CDCl$_3$) 161.5, 161.2, 137.7, 134.5, 133.1, 126.7, 116.0, 104.7, 103.7, 102.5, 98.7, 98.1, 55.6, 55.5. Calc. Analysis for $C_{20}H_{21}NO_4$: C, 70.78; H, 6.24; N, 4.13. Found: C, 70.65; H, 6.07; N, 4.20%.

Example 11

Preparation of 4-amino-3,5-bis(3,5-dimethoxyphenyl)-1H-pyrrole-2-methyl carboxylate, of the following structural formula

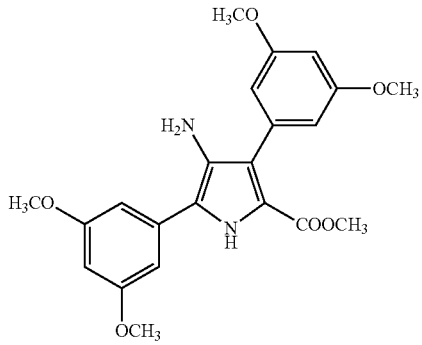

Seven milliliters (7 ml) of a SnCl$_2$2H$_2$O 1 M in DMF were added to 0.2 g (0.45 mmol) of 3,5-bis(3,5-dimethoxyphenyl)-4-nitro-1H-pyrrole-2-methyl carboxylate (Prepared as stated in Example 2) and was agitated at 50° C. for 16 hours. Upon completion of the reaction, 4.5 ml of AcOEt and 10% aqueous Na$_2$CO$_3$ solution were added until no further precipitate appeared. The organic phase was separated and washed with saturated Na$_2$CO$_3$ solution and water. After drying on anhydrous Na$_2$SO$_4$ and evaporating at low pressure, the crude portion was purified by means of pressure column chromatography (Eluent: AcOEt/hexanes) obtaining 4-amino-3,5-bis(3,5-dimethoxyphenyl)-1H-pyrrole-2-methyl carboxylate.

4-Amino-3,5-bis(3,5-dimethoxyphenyl)-1H-pyrrole-2-methyl carboxylate: Yield: 81%; p.f. 74-76° C.; IR 3417, 3346, 1678, 1597, 1211, 1151 cm$^{-1}$; $^1$H-RMN (δ ppm, CDCl$_3$) 8.74 (s, 1H), 6.74 (d, 2H, J=2.2 Hz), 6.60 (d, 2H, J=2.1 Hz), 6.46 (t, 1H, J=2.1 Hz), 6.40 (t, 1H, J=2.0 Hz), 3.84 (s, 6H), 3.81 (S, 6H), 3.73 (s, 3H); $^{13}$C-RMN (δ ppm, CDCl$_3$) 161.6, 160.6, 135.0, 133.6, 129.5, 121.6, 120.5, 116.7, 108.2, 103.7, 99.8, 99.2, 55.6, 55.5, 51.5. Calc. Analysis for $C_{22}H_{24}N_2O_6$: C, 64.07; H, 5.87; N, 6.79. Found: C, 63.91; H, 5.74; N, 6.57%.

Example 12

Preparation of 4,6-dimethoxy-2-(3,5-dimethoxyphenyl)-1H-indole, of the following structural formula

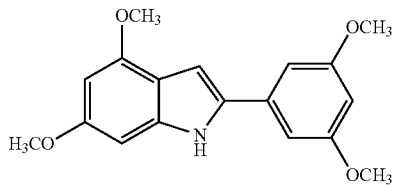

0.32 g (2.1 mmoles) of 3,5-dimethoxyaniline, 0.26 g (1.0 mmol) of 2-bromo-1-(3,5-dimethoxyphenyl)ethanone and 0.42 ml (3.3 mmol) of N,N-dimethylaniline were placed in a vial. The vial was placed inside a monomode microwave reactor and was radiated at a power of 100 W, at a temperature of 150° C. for 10 minutes. After cooling the reaction vial, the mixture was dissolved in AcOEt, was washed with an aqueous HCl 2N solution, was dried on anhydrous $Na_2SO_4$ and was evaporated at low pressure. The crude portion was purified by means of pressure column chromatography (Eluent: AcOEt/hexanes) obtaining 4,6-dimethoxy-2-(3,5-dimethoxyphenyl)-1H-indole.

4,6-dimethoxy-2-(3,5-dimethoxyphenyl)-1H-indole: Yield: 80%; p.f. 126-128° C.; IR 3407, 1608, 1206, 1161 cm$^{-1}$; $^1$H-RMN (δ ppm, CDCl$_3$) 8.18 (s, 1H), 6.82 (s, 1H), 6.73 (d, 2H, J=1.8 Hz), 6.49 (s, 1H), 6.38 (s, 1H), 6.22 (s, 1H), 3.92 (s, 3H), 3.83 (s, 9H); $^{13}$C-RMN (δ ppm, CDCl$_3$) 161.4, 158.2, 153.9, 138.3, 135.3, 134.7, 114.6, 103.1, 99.4, 97.8, 92.2, 87.1, 55.8, 55.6. Calc. Analysis for $C_{18}H_{19}NO_4$: C, 68.99; H, 6.11; N, 4.47. Found: C, 68.92; H, 5.84; N, 4.46%.

Example 13

Preparation of 4,6-dimethoxy-2-(2,5-dimethoxyphenyl)-1H-indole, of the following structural formula

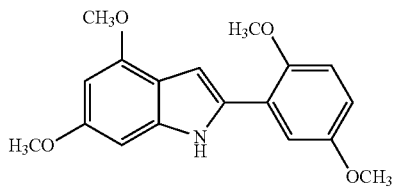

The compound stated in the heading above was prepared and purified according to a procedure similar to that described in Example 11.

4,6-dimethoxy-2-(2,5-dimethoxyphenyl)-1H-indole: Yield: 61%; p.f. 148-150° C.; IR 3407, 1542, 1487, 1211, 1141 cm$^{-1}$; $^1$H-RMN (δ ppm, CDCl$_3$) 9.62 (s, 1H), 7.32 (d, 2H, J=3.0 Hz), 6.92 (d, 2H, J=8.9 Hz), 6.90 (d, 1H, J=1.3 Hz), 6.76 (dd, 1H, J=8.9, J'=3.0 Hz), 6.52 (s, 1H), 6.21 (d, 1H, J=1.3 Hz), 3.94 (s, 6H), 3.84 (s, 3H), 3.81 (s, 3H); $^{13}$C-RMN (δ ppm, CDCl$_3$) 157.7, 154.3, 153.5, 149.9, 137.4, 133.1, 121.7, 113.5, 113.4, 112.3, 97.2, 91.7, 86.8, 56.6, 55.8, 55.7, 55.4. Calc. Analysis for $C_{18}H_{19}NO_4$: C, 68.99; H, 6.11; N, 4.47. Found: C, 68.72; H, 6.44; N, 4.45%.

Example 14

Preparation of 4,6-dimethoxy-2-(3,5-dimethoxyphenyl)-1H-indole-1-tert-butyl carboxylate, of the following structural formula

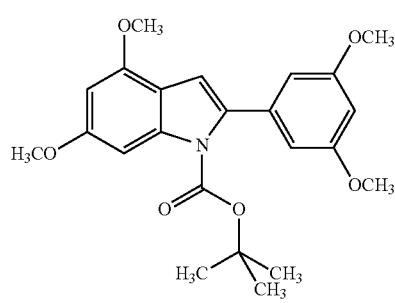

0.20 g (0.92 mmol) of Boc$_2$O and 0.009 g (0.071 mmol) of 4-dimethylaminopyridine were added to a solution of 0.21 g (0.68 mmol) of 4,6-dimethoxy-2-(3,5-dimethoxyphenyl-1H-indole (Prepared according to the procedure described in Example 11) in 8.2 ml of acetonitryl and was agitated at ambient temperature for 3 hours. In following, the solvent was evaporated at reduced pressure and the resulting product was purified by means of pressure column chromatography (Eluent: AcOEt/hexanes), obtaining the compound 4,6-dimethoxy-2-(3,5-dimethoxyphenyl)-1H-indole-1-tert-butyl carboxylate.

4,6-Dimethoxy-2-(3,5-dimethoxyphenyl)-1H-indole-1-tert-butyl carboxylate: Yield: 60%; p.f. 92-94° C.; IR 1733, 1613, 1587, 1311, 1151 cm$^{-1}$; $^1$H-RMN (δ ppm, CDCl$_3$) 7.38 (d, 1H, J=1.6 Hz), 6.59 (s, 1H), 6.54 (d, 1H, J=2.3 Hz), 6.44 (t, 1H, J=2.3), 6.35 (d, 1H, J=1.6 Hz), 3.89 (s, 3H), 3.88 (s, 3H), 3.79 (s, 6H), 1.33 (s, 9H); $^{13}$C-RMN (δ ppm, CDCl$_3$) 160.4, 159.3, 153.3, 150.6, 139.3, 137.6, 137.2, 113.8, 107.1, 106.8, 99.9, 94.8, 91.6, 83.5, 56.0, 55.6, 27.8. Calc. Analysis for $C_{21}H_{27}NO_6$: C, 66.81; H, 6.58; N, 3.39. Found: C, 66.67; H, 6.44; N, 3.44%.

Example 15

Preparation of 4,6-dimethoxy-2-(2,5-dimethoxyphenyl)-1H-indole-1-tert-butyl carboxylate, of the following structural formula

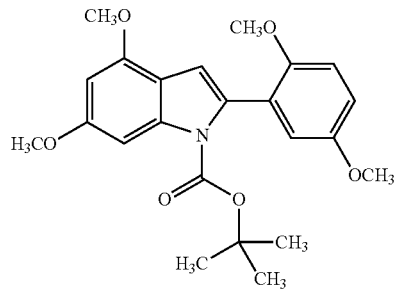

The compound stated in the heading above was prepared and purified by means of a procedure similar to that described in Example 13.

4,6-Dimethoxy-2-(2,5-dimethoxyphenyl)-1H-indole-1-tert-butyl carboxylate: Yield: 86%; p.f. 56-58° C.; IR 1783, 1497, 1311, 1221, 1151 cm$^{-1}$; $^1$H-RMN (δ ppm, CDCl$_3$) 7.39 (d, 1H; J=1.5 Hz), 6.94 (d, 1H, J=3.0 Hz), 6.84 (dd, 1H, J=8.8 Hz, J'=3.0 Hz), 6.77 (d, 1H, J=8.8), 6.54 (s, 1H), 6.33 (d, 1H, J=1.5 Hz), 3.88 (s, 6H), 3.78 (s, 3H), 3.67 (s, 3H), 1.30 (s, 9H); $^{13}$C-RMN (δ ppm, CDCl$_3$) 159.0, 153.6, 153.2, 151.7, 150.5, 138.7, 134.2, 125.9, 116.2, 113.6, 111.1, 106.5, 94.4, 91.5, 82.8, 56.0, 55.9, 55.6, 27.7. Calc. Analysis for C$_{23}$H$_{27}$NO$_6$: C, 66.81; H, 6.58; N, 3.39. Found: C, 66.81; H, 6.24; N, 3.51%.

Example 16

Preparation of 2-(2,5-dihydroxyphenyl)-1H-indole-4,6-diol, of the following structural formula

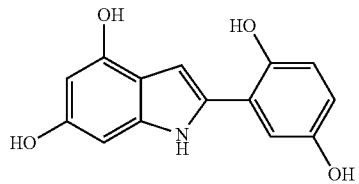

In a spherical flask cooled to 0° C. and under argon atmosphere, 0.2 g (0.5 mmol) of 4,6-dimethoxy-2-(2,5-dimethoxyphenyl)-1H-indole-1-tert-butyl carboxylate (Prepared as described in Example 14) were dissolved in 12 ml of dry dichloromethane. In following, 6 ml of BBr$_3$ (1 M in dichloromethane) were added drop by drop and agitated to ambient temperature for 16 hours. The reaction was halted by adding MeOH drop by drop at 0° C. The resulting solid was filtered and was purified by means of pressure column chromatography (Eluent: MeOH/CH$_2$Cl$_2$) obtaining the compound 2-(2,5-dihydroxyphenyl)-1H-indole-4,6-diol.

2-(2,5-Dihydroxyphenyl)-1H-indole-4,6-diol: Yield: 52%; p.f. breaks down; IR 3363, 1612, 1456, 1207 cm$^{-1}$; $^1$H-RMN (δ ppm, DMSO-d$_6$) 10.46 (s, 1H), 9.14 (s, 1H), 9.09 (s, 1H), 8.65 (s, 1H), 8.60 (s, 1H), 7.01 (d, 1H, J=2.8 Hz), 6.80 (d, 1H, J=1.3 Hz), 6.73 (d, 1H, J=8.6 Hz), 6.60 (dd, 1H, J=8.6 Hz, J'=2.8 Hz), 6.29 (s, 1H), 5.92 (d, 1H, J=1.3 Hz); $^{13}$C-RMN (δ ppm, DMSO-d$_6$) 153.9, 150.3, 149.8, 146.3, 138.4, 131.3, 119.8, 116.8, 113.8, 112.5, 112.2, 98.4, 94.5, 88.2. Calc. Analysis for C$_{14}$H$_{11}$NO$_4$: C, 65.37; H, 4.31; N, 5.44. Found: C, 65.52; H, 4.36; N, 5.11%.

Example 17

Tests Conducted to Evaluate the In Vitro and In Vivo Biological Activity of the General Formula (I) Compounds The potential antimetastatic effect of general formula (II) compounds was studied by using an in vivo experimental model of inflammation and oxidative stress-dependent hepatic colonization of intrasplenically-injected B16 melanoma (MB16) cells, in which the metastasis density and volume, the type of metastasis based on the angiogenic (sinusoidal or portal) pattern thereof, the length of the angiogenic vessels within tumor nodules, the percentage of metastatic focal points with cavitation and the percentage of in situ proliferating metastatic cells were histologically determined.

In following, for the purpose of studying in what stage of the development of the metastasis said compounds were acting, the in vivo effect thereof on the hepatic retention of the tumor cells and in vitro, on one hand, on the production of hydrogen peroxide, adhesion and proliferation of murine B16 melanoma and human A375 melanoma cells and, on the other hand, on the migration and proliferation of primary cultures of endothelial cells and hepatic estellate cells was determined.

Following an optimization of the chemical structure, the general formula (III) compounds and the general formula (IV compounds, the chemical and configurational stability of which afford the possibility of preserving the trans arrangement between the aromatic rings (A and B), see general formula (I), avoiding the possibility of isomerization and the resulting loss activity. The following in vitro tests were conducted with these compounds:

Tests of B16 (MB16) melanoma cell interaction with primary cultures of hepatic sinusoidal endothelium (HSE cells treated with conditioned MB16 (MC-MB16) media:

ELISA determination of the TNF-alpha concentration in the supernatants of HSE cell cultures treated with MC-MB16.

Determination of the production of hydrogen peroxide from HSE cells and MB16 cells.

Cell adhesion tests of MB16 cells incubated with non-toxic concentrations of hydrogen peroxide to the immobilized recombinant VCAM-1 substrate.

Proliferation tests of the MB16 cells treated with recombinant murine IL-18.

Enzymatic immunoassay (EIA) of PGE2 in the supernatant of the untreated and VEGF-treated HSE cells.

Lastly, an evaluation was made on the effect of those compounds showing greater inhibitory activity in the in vitro tests on the metastatic capacity of the MB16 cells by means of in vivo tests on the development of hepatic metastasis.

Example 17.a

Tests Conducted to Evaluate the In Vitro Biological Activity

Culture of B16 (MB16) and A375 (MA375) melanoma cells. The MB 16 (B16F10 subline) murine tumor cells were cultured at 37° C., with 5% CO$_2$ atmosphere in Dulbecco's modified Eagle's medium (DMEM)-HCO$_3$ penicillin (100 U/ml), streptomycin (100 μg/ml), supplemented with 5% fetal bovine serum and adjusted to pH 7.4. The cells were maintained and subcultured according to the method described by Vidal-Vanaclocha et al. (1994) [Vidal-Vanaclocha, F., Amézaga, C., Asumendi, A., Kaplanski, G. & Dinarello, C. A. Interleukin-1 receptor blockade reduces the number and size of murine B16 melanoma hepatic metastases. Cancer Research, 1994, 54, 2667-2672]. The conditioned media were obtained from subconfluyent cultures maintained in absence of FBS for 24 hours.

Isolation of primary murine cultures of hepatic sinusoidal endothelial (HSE) cells. The hepatic sinusoidal cells were isolated from C57BL/6J mice (males, aged 6-8 weeks) supplied by IFFA Credo (L'Arbreole, France), followed by a purification and identification of the HSE cells following the protocol described by Vidal-Vanaclocha et al. (1993) [Vidal-Vanaclocha, F., Rocha, M., Asumendi, A. & Barbera-Guillem, E. Isolation and enrichment of two sublobular compartment-specific endothelial cell subpopulations from liver sinusoids. Hepatology, 1993, 18, 328-339]. Stable primary cultures of HSE cells were obtained after seeding the cells on a type I collagen substrate (Sigma Chemicals Co, St Louis, Mo.), and the cultures were maintained in DMEM-$HCO_3^-$, penicillin (100 U/ml), streptomycin (100 µg/ml), supplemented with 10% fetal bovine serum at 37° C. with 5% CO2 in atmosphere at 98% humidity.

isolation of primary human cultures of hepatic sinusoidal endothelial (HSE) hepatic stellate cells (HSCs). The primary cultures of human HSE and HSC cells were obtained by non-tumoral hepatic tissue serial profusion with collagenase and pronase solutions, followed by Nycodenz gradient and seeded on 24-well plates ($0.5 \times 10^4$ cells/$cm^2$) in DMEM. supplemented with 10% FBS.

MB16 cell adhesion to the monolayer of HSE cells in culture. The endothelial cells were isolated 24 hours prior to the adhesion test and were seeded on 24-well plate, maintaining them a minimum of 4 hours in serum-free medium before incubating them with DMEM in the presence or not of MC-MB16 for 8 hours. The synthesized compounds (JE2:2 see FIG. 6; JEM2:2-01 and JEM2:1-02 see FIG. 8A; YEF02, YEF03, YEF07, YEF05B, YEF07B and YEF05H see FIG. 10) were added to a 2.5 µM concentration prior to the MC-MB16. On the other hand, the MB16 cells were marked with 40 µg/ml from the fluorescent probe BCECF-AM (carboxyfluorescein, 2',7'-bis-(2-carboxy-ethyl)-5-(6)carboxyfluorescein aminoxymethyl ester) supplied by Molecular Probes Inc. (Oregon, USA). Afterward, a washing process was performed with DMEM-$HCO_3^-$—to remove the excess fluorochromium, the number of viable cells being calculated by means of the trypan blue exclusion test and resuspended to a concentration of $2 \times 10^5$ cells/ml. Lastly, 1 ml of the MB16 cell suspension was added to each well on the primary HSE cell culture plate. The co-culture plates were incubator-incubated at 37° C. for 8 minutes. The percentage of cellular adhesion was calculated by means of the a fluorescence measurement system described by Vidal-Vanaclocha et al. (1994) [Vidal-Vanaclocha, F., Amézaga, C., Asumendi, A., Kaplanski, G. & Dinarello, C. A. Interleukin-1 receptor blockade reduces the number and size of murine B16 melanoma hepatic metastases. Cancer Research, 1994, 54, 2667-2672]. In the experiments with IL-18, the MB16 cells were incubated with 10 ng/ml of IL-18 for 4 hours prior to being marked with BCECF-AM and were adhered to the HSE cell plate. The results in the figures are given as values related to the adhesion percentages of the untreated HSE cells.

MB16 and MA375 cell adhesion to immobilized VCAM-1 substrates. The MB16 and MA375 cell adhesion tests were conducted on immobilized VCAM-1 substrates (2 µg/ml of recombinant human VCAM-1, R&D Systems, Minneapolis, Minn.) on 96-well plates. To avoid non-specific attachment to the plastic, 0.5% BSA dissolved in PBS was added to the wells for 2 hours at ambient temperature prior to conducting the adhesion test. The melanoma cells were preincubated with 2.5 µM of the compounds to be tested (azaresveratrol, see Table 2; JE1:2, JE2:1 and JE2:2 see FIG. 2; JEM2:2-01 and JEM2:1-02 see FIG. 7; YEF02, YEF03, YEF07, YEF05B, YEF07B and YEF05H. see FIG. 9) for 30 minutes, to which 10 µM of hydrogen peroxide or 10 ng/ml of IL-18 were added, respectively for a further 24 hours. Afterward, the cells were washed and marked with the BCECF-AM fluorescent probe (carboxyfluorescein, 2',7'-bis-(2-carboxy-ethyl)-5-(6)carboxyfluorescein aminoxymethyl ester). Thirty minutes later, a washing process was performed to remove the excess fluorochromium, the number of viable cells being calculated by means of the trypan blue exclusion test and ($5 \times 10^4$ cells/well) being added to the 96-well plate. The co-culture plates were incubator-incubated at 37° C. for 1 hours. The percentage of cellular adhesion was calculated by measuring the fluorescence emitted by the adhered cells (obtained after washing the plate) with regard to the fluorescence emitted by the total number of cells added. The results in the figures are given in values related to the adhesion percentages of the untreated melanoma cells.

ELISA determination of the TNF-alpha concentration in the supernatant from MC-MB16-treated HSE cells. Primary cultured HSE cells were incubated in the presence or absence of 2.5 µM of the synthesized compounds (JEM2:2-01 and JEM2:1-02 see FIG. 8B) for 30 minutes, after which MB16-conditioned media were added. Eight (8) hours later, the supernatant from cultured endothelial cells were collected, filtered through 0.22 µm membranes and the concentration of TNF-alpha was then assayed using the ELISA test (R&D Systems).

Determination of hydrogen peroxide production from HSE and MB16 cells. Primary cultures of HSE cells were treated with 10 µg/ml of the DCFH-DA fluorescent probe for 30 minutes at 37° C. and were washed to eliminate the excess fluorochromium. Afterward, fresh culture medium was added thereto in the presence or absence of 2.5 µM of the compounds JE1:2, JE2:1 or JE2:2 and the production of $H_2O_2$ over the course of time was determined (see FIG. 5). The hydrogen peroxide produced by the cells oxidizes the probe, converting it into a fluorescent molecule. Thus, the cell fluorescence produced by the accumulation of DCF made it possible to detect the intracellular production of hydrogen peroxide. In each cell well, it was possible to determine the relative fluorescence value (arbitrary units of fluorescence brightness) in relation to the quantity of hydrogen peroxide produced at different incubation times. In the experiments with MB16 cells, once the cells had been marked with the DCFH-DA probe, they were incubated for 300 minutes with 2.5 µM of the azaresveratrol or JE2:2 compounds, 10 ng/ml of IL-18 (FIG. 4) then having been added.

In vitro Melanoma cell proliferation test. The MB16 or MA375 cells are seeded (2500 cells/well/200 µl) in DMEM medium (Dulbecco's modified Eagle's medium) with 10% fetal bovine serum (FBS). Once adhered, they were washed to remove the FBS and fresh medium was added in the presence or absence of 2.5 µM of the compounds to be tested. In the experiments with MA375, the compound azaresveratrol (see Table 4) was used, and in the experiments with MB16 cells, the compounds azaresveratrol, JE1:2, JE2:1 or JE2:2 (see FIG. 3) were used. Thirty (30) minutes later, 10 ng/ml of IL-18 or HSC-conditioned media (murines in the case of B16 and human ones in the case of A375) were added to some wells, and the plates were incubated for 48 hours at 37° C. with 5% $CO_2$ Upon completion of the incubation period, the cells were fixed with 64% for 1 hours, were washed and were allowed to dry in the incubator at 50° C. for 30 minutes. In following, 100 µl/well of sulforhodamine 101 (0.4% p/v) was added and they were incubated at room temperature in the dark for 30 minutes. After washing, 200 µl/well of Tris base 10 mM pH 10.5 was added and the fluorescence was measured by means of a 530 nm, 620 nm emission excitation filter plate fluorescence reader. The number of cells was calculated by extrapolating said fluorescence data on a standard straight line previously obtained based on the fluorescence emitted in an increasing number of cells.

TABLE 4

| IN VITRO TESTS | CONTROL | TREATMENT | +RESVERATROL | +AZARESVERATROL |
|---|---|---|---|---|
| Proliferation of MA375 cells in response to human HSC soluble factors (No. cells per well) | 9000 ± 60 | 17500 ± 50 | 9050 ± 100 | 9250 ± 65 |
| Proliferation of MB16 cells in response to murine HSC soluble factors (No. cells per well) | 16300 ± 300 | 21660 ± 500 | 16800 ± 250 | 16750 ± 135 |

HSC proliferation test. Primary cultured human HSC cultures were seeded (2500 cells/well/200 µl) in DMEM with 10% FBS. Once adhered, they were washed to remove the FBS and were incubated with fresh medium in the presence or absence of 12.5 µM of the azaresveratrol compound (see Table 3). Thirty (30) minutes later, conditioned media obtained from MA375 cells were added to some wells, and the plates were incubated for 48 hours in humid incubator at 37° C. with 5% $CO_2$. Upon completion of the incubation time, the cells were fixed and were processed for counting just as previously described hereinabove.

PGE2 determination in HSE cell supernatants (see FIG. 11). Primary cultured HSE cells were incubated in the presence or absence of increasing concentrations (1, 2.5 and 10 µM) of the compounds JE2:2, YEF07 and YEF05B for 30 minutes. In following, 10 ng/ml of recombinant murine VEGF or the same volume of saline solution was added, 4 hours after which supernatants were collected and the PGE2 concentration determined by enzymatic immunoassay (EIA) supplied by Amersham Biosciences (Uppsala, Sweden).

Human HSC and HSE cell migration tests (see Table 3). Primary cultured hepatic endothelial cells ($25 \times 10^5$) or hepatic stellate cells ($2 \times 10^4$) were seeded in the upper compartment of modified Boyden chambers equipped with a polycarbonate filter of an 8 µm pore size. Some cells were incubated in the presence or absence of 12.5 µM of azaresveratrol, 30 minutes prior to adding conditioned tumor medium. Twenty-four (24) hours later (in the case of the endothelial cells) or 4 hours later (in the case of hepatic star cells) the number of cells having passed through the membrane was determined. The cells were fixed, were stained with hematoxylin eosine and were counted under the microscope (20×) in 5 fields per well.

Example 17.b

Tests Conducted to Evaluate the In Vivo Biological Activity

MB16 Hepatic Metastasis Test using C57 BL/6J mice (males 6-8 weeks of age) supplied by IFFA Credo (L'Arbreole, France). The care, maintenance and experimental conditions were carried out in accordance with that which is set forth under EEC Council Directive 86/609 (OJ L 358. 1, Dec. 12, 1987) and the NIH guide for the care and use of laboratory animals (NIH publication 85-23, 1985). In the experiments with the resveratrol and azaresveratrol compounds (Table 1), the animals (10 per group) received 1 mg/Kg/day of the compounds nasogastrically every day up to the time of sacrifice. In the experiments with the JE2:2 compound (FIG. 12), one group of mice (n=10) was given an intraperitoneal injection of 0.5 mg/kg of the JE2:2 compound dissolved in 0.1 ml of PBS. The control group (n=10), was given an intraperitoneal injection of PBS. One hour later, animals were anesthetized and were intrasplenically injected with MB16 cells ($3 \times 10^5$ cells/mouse). The same treatments, at the same doses, were repeated on days 2, 3, 4, 8, 9, 10 and 11 following tumor injection.

Twelve (12) days later, the livers were removed and processed for the histological study. Firstly, they were fixed in a solution of zinc (0.5 g calcium acetate, 5 g zinc acetate, 5 g zinc chloride and 1000 ml tris buffer, pH 7.4) for 24 hours. Once fixed, they were dehydrated in alcohols of increasing concentrations, and paraffin block were included. Afterward, a minimum of nine (9) cuts 10 µm in thickness were made per liver, leaving a space of 300 µm between every 3 cuts and a 1 mm space between successive groups of 3 cuts. Once the

TABLE 3

| IN VITRO TESTS | CONTROL | TREATMENT | +RESVERATROL | +AZARESVERATROL |
|---|---|---|---|---|
| Migration of human HSC's treated with MC-MA375 (No. cells migrated per field) | 10.0 ± 4 | 91.5 ± 19 | 6.5 ± 1.4 | 6.0 ± 1.3 |
| Proliferation of human HSC's treated with MC-MA375 (No. cells per well) | 2550 ± 22 | 4400 ± 30 | 2250 ± 100 | 2600 ± 60 |
| Migration of HSE's treated with MC-MA375 (No. cells per field) | 10.0 ± 4 | 35.0 ± 8.0 | 13.5 ± 5.0 | 15.5 ± 30 | sections had been obtained, they were processed and stained with hematoxylin-eosine. On the one hand, the number, mean diameter, area and position coordinates of each metastasis were quantified by means of an integrated image analysis system (Olympus Microimage 4.0 capture kit) connected to an Olympus BX51TF microscope. With obtained data, metastatic parameters (that is to say, the number of focal points per 100 $mm^3$ of hepatic tissue) and metastatic volume (that is to say, the volume of liver occupied by metastatic tissue) were calculated as described by Vidal-Vanaclocha et al. [cf. Vidal-Vanaclocha, F., Amézaga, C., Asumendi, A., Kaplanski, G. & Dinarello, C. A. "Interleukin-1 receptor blockade reduces the number and size of murine B 16 melanoma hepatic metastases", *Cancer Research*, 1994, vol. 54, pp. 2667-2672]. On the other hand, more cuts were made in the same blocks, and a double marking with CD31 and desmine was performed to calculate the number and length of the angiogenic vessels within the metastases and also to study metastases according to their angiogenic pattern in portal-type expansive metastases (the angiogenic vessels surround the metastases) or sinusoidal type invasive metastases (containing an internal network of angiogenic capillaries). Another parameter that was quantified is the cavitated metastasis percentage. Lastly, immunohistochemical detection of Ki67 antigen was performed to assess the number of tumor cells which proliferated per unit of tumor surface.

Test of hepatic retention of luciferase-transfected MB16 cells (MB16-Luc) (see Table 1). B16M Cells were stably transfected by lipofection as described previously (Rubio N, Martinez-Villacampa M, Blanco J. Traffic to lymph nodes of PC-3 prostate tumor cells in nude mice visualized using the luciferase gene as a tumor cell marker. Lab Invest 1998; 78:1315-1325), using plasmid pRc/cytomegalovirus-luciferase, a construct containing the *Photinus pyralis* luciferase gene coding sequence under transcriptional control of the cytomegalovirus promoter and the neomycin resistance gene to the G418 antibiotic (Sigma Chemicals Co.). A total of 300,000 viable B16M-Luc cells were intrasplenically injected into C57BL/6J mice (10 mice per group) which had previously been nasogastrically administered 2 doses of 1 mg/kg/day of compound to be tested. One group of mice received resveratrol, the other group of mice received azaresveratrol. The group of control mice were administered the same solution of the compounds. All mice were killed by cervical dislocation 18 h later and the livers were processed as described previously (Rubio et al, 1998) to measure luciferase activity by chemiluminescence using the standard luciferase assay kit (Promega Co., Madison, Wis.) as reported (Rubio et al, 1998). Production of light was measured using a luminometer designed to read individual samples tubes (bioorbit, LKB Wallac; Turku, Finland) after the addition of 100 µl of luciferase assay reagent to 20 µl of each liver homogenate. Light detector measurements were expressed in relative light units, which were proportional to photon numbers. Linearity and sensitivity of light detection in liver homogenates and influence of hepatic microenvironment on luciferase activity of B16M-Luc were also evaluated as described previously (Rubio et al, 1998).

TABLE 1

| IN VIVO TESTS | CONTROL | +RESVERATROL | +AZARESVERATROL |
|---|---|---|---|
| Hepatic retention of MB16 Luc cells (No. cells × $10^6$) | 1.80 ± 0.23 | 1.05 ± 0.3 | 0.98 ± 0.24 |
| Hepatic focal point density (No. focal points/100 $mm^3$) | 60.0 ± 11 | 30.0 ± 11 | 28.0 ± 10 |
| No. portal metases/No. sinusoidal metastasis | 30/30 (1) | 22.5/7.5 (3) | 22.5/5.5 (4.09) |
| Volume of hepatic metastasis ($mm^3$) | 60.0 ± 7.5 | 18.7 ± 7.5 | 24.0 ± 9.0 |
| Length of angiogenic vessels (µm) | 175.0 ± 10 | 88.0 ± 23 | 88.0 ± 21 |
| Percentage of focal points w/cavitation (% of total no. of metastatic focal points) | 13.5 ± 5.0 | 41.5 ± 11 | 40.0 ± 10 |
| Metastatic cell proliferation index (% cells positive to Ki67 antigen) | 71.0 ± 5.0 | 40.0 ± 5.0 | 35.0 ± 10 |

Example 17. c

General Formula (II) Compound Biological Activity Results

In Vivo Test Results:

Firstly, a comparative study was made between the effect of the resveratrol and the general formula compound (azaresveratrol) on the intrasinusoidal retention of the tumor cells throughout the first 18 hours and their capacity to develop metastasis on day 12 following their inoculation (see Table 1).

Both treatments significantly ($P<0.05$) reduced the intrahepatic retention of tumor cells 18 hours following their injection. These retention experiments were conducted with MB16 cells transfected with the lucerifase gene (MB16-Luc precisely as previously described in the methods employed. In addition thereto, the daily administration of 1 mg/Kg/day of resveratrol and azaresveratrol nasogastrically reduced the mean density of hepatic metastases by 50% and 46%, respectively, which denotes a statistically significant ($P<0.01$) antimetastatic effect in comparison to the control animals. The immunohistochemical staining for CD31 and desmine revealed that the treatments affected to a greater degree the metastases with a sinusoidal-type angiogenic pattern, also known as invasive metastases, whilst they had almost no effect on the number of metastases having a portal-type angiogenic pattern, or expansive metastases. On the other hand, the percentage of hepatic volume occupied by metastatic tissue decreased by 40% in the treated animals. Said inhibition in the volume had a reduction in the length of angiogenic vessels, a larger percentage of metastatic foci with internal cavitation and a lower tumor cell proliferation index as determined by immunohistochemistry for Ki67 antigen (see Table I). These results prove, on one hand, that the general formula compound (azaresveratrol) has an in vivo antimetastatic efficiency similar to natural resveratrol and, on the other hand, that the effect is two-way, affecting both the stroma as well as the tumor cells directly.

In Vitro Test Results:

In following, a series of in vitro tests are conducted for identifying the mechanisms of action of the azaresveratrol on the different stages of the development of the metastases. The results are compared in relation to those obtained with resveratrol.

Table 2 shows that the preincubation of the MB16 cells with 2.5 µM of resveratrol and azaresveratrol for 30 minutes prior to adding IL-18 significantly (P<0.01) inhibited the increase of both the percentage of adhesion of tumor cells to the HSE and the production of tumoral H2O2 in response to IL-18. Not statistically significant differences were found between the two compounds. Likewise, this inhibitory effect was also observed in adhesion tests of A375 human melanoma cells incubated with 10 µM H2O2 for 2 hours or with 1 ng/ml IL-18 for 6 hours to immobilized VCAM-1 substrates. Therefore, the azaresveratrol inhibited early processes to the metastatic implantation such as tumoral adhesion to the vascular endothelium.

To determine whether the compounds affect mechanisms associated with metastatic development and growth, migration tests are conducted on primary human cultures of hepatic stellate cells (HSC) and hepatic sinusoidal endothelial cells (HSE) in response to soluble factors from MA375 cells (see Table 3). When the HSE and HSC cells were administered 12.5 µM both of resveratrol and azaresveratrol 30 min prior to the MC-A375, the increase in migration induced by the tumor was abolished. On the other hand, the same treatment abrogated the increase in HSC proliferation in response to the inhibition of the migration of HSE cells and HSCs as well as of the proliferation of the latter of the two explains the antiangiogenic effect of the compounds observed in the in vivo experiments.

An evaluation was also carried about to determine the direct effect of the resveratrol and azaresveratrol on the proliferation of B16 and A375 cells in response to soluble factors secreted by HSCs. As shown in Table 4, the treatment with MC-CEH for 48 hours significantly (P<0.01) increased the proliferation of melanoma cells. This increase in the proliferation was prevented by incubating the cells with 2.5 µM of both resveratrol and azaresveratrol for 30 minutes before adding the MC-CEH's.

with the JE1:2, JE2:1 and JE2:2 compounds significantly (P<0.01) inhibits the increase in the percentage of H2O2-treated melanoma cell adhesion to the immobilized VCAM-1. The JE2:2 compound is the one showing the greatest inhibitory effect.

In the proliferation tests (see FIG. 3), the treatment with 10 ng/ml of the proinflammatory cytokine IL-18, produced a statistically significant (P<0.01) increase in the number of MB16 cells in relation to the cells receiving basal medium. Once again, the pretreatment with JE1:2, JE2:1 and JE2:2 compounds reduced said increase and confirms that the JE2:2 compound as being the most highly effective. All of the determinations are made in triplicate.

Later, for the purpose of proving the antioxidant effect of the JE2:2 compound, tests were conducted on H2O2 production by MB16 cells in response to recombinant Il-18. See FIG. 4, where the treatment with the JE2:2 compound inhibited the production of H2O2 of cells in basal conditions and completely abrogated (P<0.01) the increase in H2O2 caused by Il-18.

Because $H_2O_2$ released by the hepatic sinusoidal endothelium (HSE) facilitated the adhesion of melanoma cells and the development of hepatic metastasis, an additional evaluation was accomplished on the effect of the compounds on tumor-activated HSE cells. As shown in FIG. 5, pretreatment of HSE with the JE2:2 compound at a concentration of 2.5 µM inhibited endothelial production of H2O2 and significantly (P<0.01) reduced the increase in adhesion of MB16 cells to the HSE activated by soluble factors of the melanoma (see FIG. 6).

It was also checked whether any of the intermediary compounds in the chemical synthesis of the JE2:2 compound also has the capacity to inhibit tumor cell adhesion. Two of the compounds, called JEM2:2-01 and JEM2:1-$O_2$ are tested. On the other hand, the preincubation of the MB16 cells with 2.5 µM of the JEM2:2-01 compound completely abrogated the increase in tumor cell adhesion to immobilized VCAM-1 induced by H2O2 (see FIG. 7). On the other hand, tumor adhesion to HSE cells treated with MC-MB16 in the presence

TABLE 2

| IN VITRO TESTS | CONTROL | TREATMENT | +RESVERATROL | +AZARESVERATROL |
|---|---|---|---|---|
| Adhesion of MB16 cells treated with IL-18 to HSE cells (% adhered cells) | 24.4 ± 4 | 54 ± 6.0 | 30 ± 4.0 | 31 ± 4.0 |
| $H_2O_2$ production by MB16 cells treated with IL-18 | 16.0 ± 3 | 34 ± 3.0 | 12 ± 1.0 | 10 ± 2.0 |
| Adhesion of MA375 cells with $H_2O_2$ to immobilized VCAM-1 (% cells adhered) | 21.0 ± 4 | 41.3 ± 4.2 | 6.5 ± 0.5 | 4.5 ± 0.3 |
| Adhesion of MA375 cells treated with IL-18 to immobilized VCAM-1 (% cells adhered) | 21.0 ± 4 | 31.5 ± 3.2 | 5.5 ± 0.4 | 5.0 ± 0.3 |

Example 17. d)

Biological Activity Results for General Formula (III) and (IV) Compounds

In Vitro Test Results:

Firstly, the effect of the formula (III) compounds on the prometastatic behavior of the tumor cells was studied. In FIG. 2, it was observed that the preincubation of the MB16 cells of both of these two compounds was determined. In FIG. 8A, both compounds, JEM2:2-01 and JEM2:1-02, significantly (P<0.01) reduced the proadhesive response induced in the HSE cells by soluble factors from MB16. A greater inhibition was observed with JEM2:2-01 compound, indicating that it is the only one which completely abrogated the inflammatory response of the endothelium, given that it inhibits the endothelial production of TNF-alpha induced by the MB-MB16 (see FIG. 8B).

Next, a screening procedure was carried out among the general formula (IV) compounds based on the in vitro tests on H2O2-treated MB16 cell adhesion to immobilized VCAM-1 or to monolayers from primary cultured HSE cells preincubated or not with MC-MB16. All of the compounds tested (YEF02, YEF03, YEF07, YEF05B, YEF07B and YEF05H) significantly (P<0.01) inhibited the increase in adhesion of MB16 cells to immobilized VCAM-1 substrate induced by treatment with H2O2 (see FIG. 9) and also significantly (P<0.01) reduced the proadhesive response of HSE to soluble factors from MB16 cells (see FIG. 10).

Given that the antimetastatic effect of many natural antioxidants, such as resveratrol, is attributed to the capacity thereof to inhibit cyclooxigenases, an EIA was then conducted to determine PGE2 concentration secreted by HSE cells incubated in the presence or absence of the synthetic compounds and treated or not with VEGF. The compounds tested are those showing a greater inhibitory effect in the previous experiments, in other words, the JE2:2, YEF07 and YEF05B compounds (see FIG. 11). All of the compounds significantly inhibited the increase in the endothelial secretion of PGE2 produced after incubating the HSE cells with 10 ng/ml VEGF for 4 hours. The inhibitory effect was also observed in some cases with the cells cultured under basal conditions. With the concentrations tested, a dose-response was solely observed with the JE2:2-compound in the presence of the VEGF. Therefore, the synthesized compounds are somehow regulating the activity of the cyclooxigenases.

In Vivo Test Results:

In following, as study was made as to the in vivo antimetastatic capacity of the JE2:2 compound by selecting it as the leading compound of the families studies both for its inhibitory activity of all of the parameters studied in vitro as well as for its being highly water-soluble. To this end, the MB16 cells were intrasplenically injected in C57BL/6J mice ($3 \times 10^5$ viable cells per animal resuspended in endotoxin-free sterile saline solution), 12 days after which the capacity thereof of development metastasis was determined.

One group of mice (n=7) were administered an intraperitoneal injection of JE2:2 (2.5 mg/kg) 1' hour prior to tumor cell injection, and the same dose was repeated on days 2, 3, 4, 8, 9, 10 and 11 in following thereto. The group of control mice (n=7) was administered PBS.

As is shown in FIG. 11, the treatment with JE2:2 reduced the mean density of hepatic metastasis by 87% and the volume occupied by metastatic tissue by 90%, which meant a statistically significant (P<0.01) antimetastatic effect in comparison to the control mice administered PBS.

The invention claimed is:

1. A compound of the formula 5-((E)-(4-Hydroxyphenylimino) methyl)benzene-1,3-diol.
2. A method for obtaining the compound according to claim 1, comprising the following steps:
    i) reacting an aromatic with an aniline in the presence or absence of an organic solvent; and
    ii) purification by crystallization in a suitable solvent.
3. A method according to claim 2, wherein a drying agent is added to the reaction mixture.
4. A pharmaceutically-acceptable composition comprising the compound according to claim 1.
5. A method of treatment of hepatic metastasis comprising administering a composition according to claim 4.
6. A pharmaceutical composition according to claim 4, in conjunction with at least one pharmaceutically-acceptable vehicle.
7. A pharmaceutical composition according to claim 4, comprising at least one additional therapeutically active substance.
8. A pharmaceutical composition according to claim 7 wherein the additional therapeutically active substance is quercetin.
9. A method of treatment of melanoma comprising administering a composition according to claim 4.

* * * * *